United States Patent
Chen et al.

(10) Patent No.: US 7,244,567 B2
(45) Date of Patent: Jul. 17, 2007

(54) DOUBLE ENDED SEQUENCING

(75) Inventors: Yi-Ju Chen, New Haven, CT (US); John H. Leamon, Guilford, CT (US); Kenton L. Lohman, Guilford, CT (US); Michael T. Ronan, New Haven, CT (US); Jonathan M. Rothberg, Guilford, CT (US); Maithreyan Srinivasan, Branford, CT (US); Michael P. Weiner, Guilford, CT (US)

(73) Assignee: 454 Life Sciences Corporation, Branford, CT (US)

( * ) Notice: Subject to any disclaimer, the term of this patent is extended or adjusted under 35 U.S.C. 154(b) by 542 days.

(21) Appl. No.: 10/768,729

(22) Filed: Jan. 28, 2004

(65) Prior Publication Data

US 2006/0134633 A1   Jun. 22, 2006

Related U.S. Application Data

(60) Provisional application No. 60/497,985, filed on Aug. 25, 2003, provisional application No. 60/476,602, filed on Jun. 6, 2003, provisional application No. 60/476,592, filed on Jun. 6, 2003, provisional application No. 60/476,504, filed on Jun. 6, 2003, provisional application No. 60/476,313, filed on Jun. 6, 2003, provisional application No. 60/465,071, filed on Apr. 23, 2003, provisional application No. 60/443,471, filed on Jan. 29, 2003.

(51) Int. Cl.
*C12Q 1/68* (2006.01)
*C12P 19/34* (2006.01)

(52) U.S. Cl. .......................... 435/6; 435/91.1
(58) Field of Classification Search .............. None
See application file for complete search history.

(56) References Cited

U.S. PATENT DOCUMENTS

| 4,994,372 | A | | 2/1991 | Tabor et al. |
| 5,436,143 | A | | 7/1995 | Hyman |
| 5,512,439 | A | | 4/1996 | Hornes et al. |
| 6,124,100 | A | * | 9/2000 | Jin ................................ 435/6 |
| 2005/0130173 | A1 | * | 6/2005 | Leamon et al. ................ 435/6 |

OTHER PUBLICATIONS

Murphy et al. Simultaneous sequencing of multiple polymerase chain reaction products and combined polymerase chain reaction with cycle sequencing in single reactions. Amer. J. Pathol. (2002) 161:27-33.*
Wiemann et al. "Doublex" fluorescent DNA sequencing: two independent sequences obtained simultaneously in one reaction with internal labeling and unlabeled primers. Anal. Biochem. (1996) 234:166-174.*
Ronaghi et al. Analyses of secondary structures in DNA by pyrosequencing. Anal. Biochem. (1999) 267:65-71.*
Ronaghi et al. (1996). *Anal. Biochem.* 242: 84-89.
Sanger et al. (1977). *Proc. Natl. Acad. Sci. U.S.A.* 74: 5463-5467.

* cited by examiner

*Primary Examiner*—Jeffrey Fredman
*Assistant Examiner*—David C. Thomas
(74) *Attorney, Agent, or Firm*—Ivor R. Elrifi, Esq.; Mintz Levin Cohn Ferris Glovsky and Popeo PC

(57) ABSTRACT

This invention relates to methods of sequencing DNA. More specifically, this invention relates to methods of sequencing both the sense and antisense strands of DNA through the use of blocked and unblocked sequencing primers. In brief, these methods include the steps of annealing an unblocked primer to a first strand of nucleic acid; annealing a second blocked primer to a second strand of nucleic acid; elongating the nucleic acid along the first strand with a polymerase; terminating the first sequencing primer; deblocking the second primer; and elongating the nucleic acid along the second strand.

35 Claims, 12 Drawing Sheets

FIG. 9A
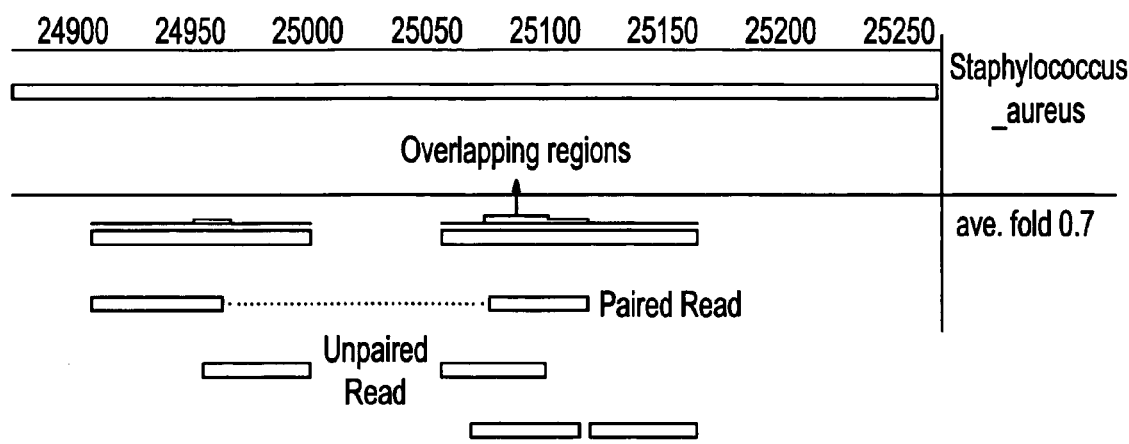
FIG. 9B
| Total Reads | 31,785 |
|---|---|
| Total 1st Strand | 15,770 |
| Total 2nd Strand | 16,015 |
| | |
| Paired | 11,799 |
| Non Paired Reads | 8,187 |
| Total Coverage | 38% |
FIG. 10
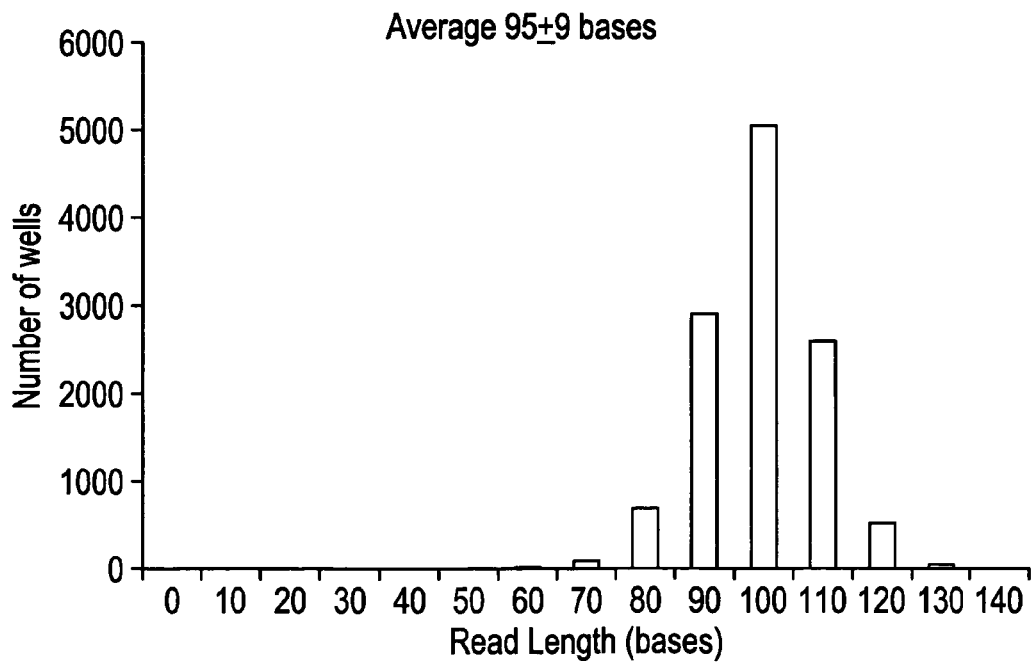

FIG. 11

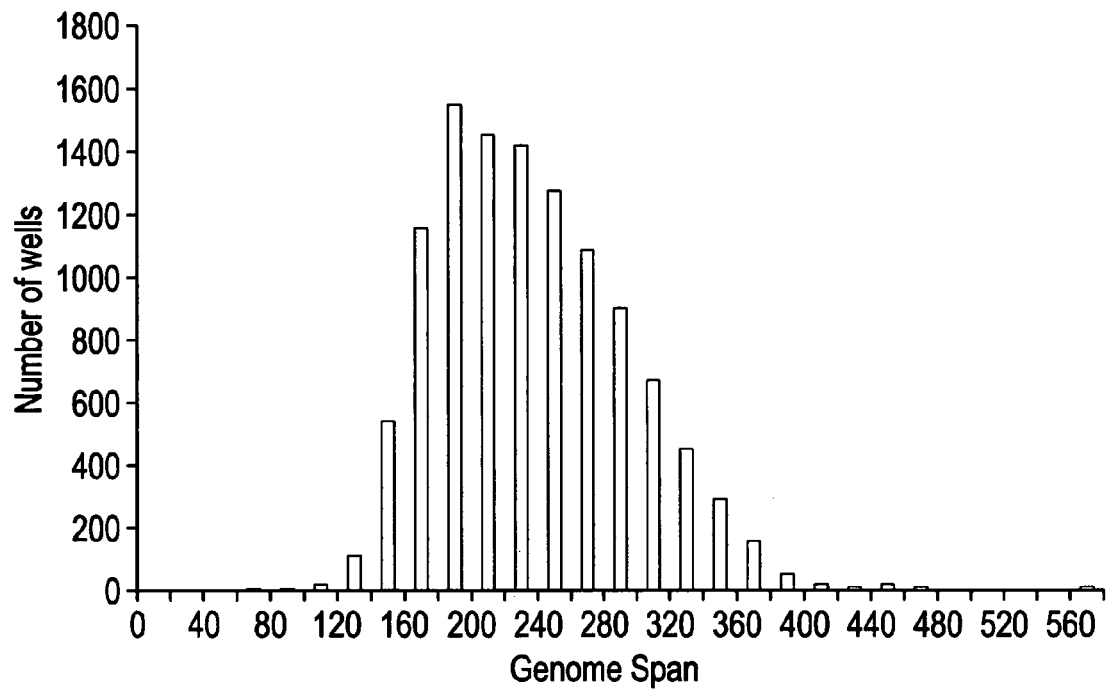

FIG. 12

| Well | Genome Position | Orientation | Alignment String |
|---|---|---|---|
| 00364_0548_2509 | 571366 | F | TATTGTTGATGCTGTAAAAaGAAGCTACTGGTGTAGtATTTTTATGAAGTT |
| 00364_0548_2509_D2 | 571512 | R | TGCTCAAAGAATTCATTTAAAATATGACCATATTTCATTGTATCTTT |
| 00383_0985_2232 | 1487890 | R | AAGCGAACAGTCAAGTACCACAGTCAGTTGACtTTTACACAAGCGGAT |
| 00383_0985_2232_D2 | 1487769 | F | TACAGGTGTTGGTATGCCATTTGCGATTTGTTGCGCTTGGTTAGCCG |
| 00397_0940_2923 | 2611033 | F | AACATATAAACATCCCCTATCTCAATTTCCGCTTCCATGTAaCAAAAAAAGC |
| 00397_0940_2923_D2 | 2611164 | R | TAGATATCACTTGCGTGTTACTGGTAATGCAGGCATGAG |
| 00417_0611_1933 | 122001 | R | ATTCAACTCTGGAAATGCtTTCTTGATACGCCTCGATGATG |
| 00417_0611_1933_D2 | 121930 | F | GATGAGGAGCTGCAATGGCAATGGGTTAAAGGCATCATCG |
| 00434_0595_0993 | 2022591 | R | TGTATCTCGATTTGGATTAGTTGCtTTTTGCATCTTCATTAGACC |
| 00434_0595_0993_D2 | 2022473 | F | CATTAACATCTGCACCAGAAATAGCTTCTAATACGATTGC |
| 00443_1003_0754 | 107373 | F | GCGACGACGTCCAGCTAATAACGCTGCACCTAAGGCTAATGATAAT |
| 00443_1003_0754_D2 | 107502 | R | AAACCATGCAGATGCTAACAAAGCTCAAGCATTACCAGAAACT |
| 00454_1257_3047 | 59038 | R | TGTTGCTGCATCATAATTTAATACTACATCATTTAAtTCTTTGG |
| 00454_1257_3047_D2 | 58880 | F | GCAGATGGTGTGACTAACCAAGTTGGTCAAAATGCCCTAAATACAAAAGAT |

DOUBLE ENDED SEQUENCING

RELATED APPLICATIONS

This application claims the benefit of priority to the following applications: U.S. Ser. No.: 60/476,602, filed Jun. 6, 2003, entitled Method For Preparing Single-Stranded DNA Libraries, U.S. Ser. No.: 60/476,504, filed Jun. 6, 2003, entitled Bead Emulsion Nucleic Acid Amplification, U.S. Ser. No.: 60/443,471, filed Jan. 29, 2003, entitled Double Ended Sequencing, U.S. Ser. No.: 60/476,313, filed Jun. 6, 2003, entitled Double Ended Sequencing, U.S. Ser. No.: 60/476,592, filed Jun. 6, 2003, entitled Methods Of Amplifying And Sequencing Nucleic Acids, U.S. Ser. No.: 60/465,071, filed Apr. 23, 2003, entitled Massively Parallel High Throughput, Low Cost Sequencing, and U.S. Ser. No.: 60/497,985, filed Aug. 25, 2003, entitled A Massively Parallel PicoTiterPlate-Based Platform For Discrete Picoliter-Scale Polymerase Chain Reactions.

This application incorporates by reference the following copending U.S. patent applications: application entitled "Method For Preparing Single-Stranded DNA Libraries", filed Jan. 28, 2004 with a serial number PCT/US04/02571, application entitled "Bead Emulsion Nucleic Acid Amplification", filed Jan. 28, 2004 with a serial number to be assigned, PCT/US04/02571 and application entitled "Methods Of Amplifying And Sequencing Nucleic Acids", filed Jan. 28, 2004 with a serial number PCT/US04/02570.

All patents and patent applications referred to in this application are hereby fully incorporated by reference.

FIELD OF THE INVENTION

This invention relates to methods for sequencing both the sense and antisense strands of a nucleic acid.

BACKGROUND

The present invention relates to a method for the base sequencing of deoxyribonucleic acid (DNA). More specifically, this invention relates to methods of sequencing both the sense and antisense strands of DNA through the use of blocked and unblocked sequencing primers.

Genome sequencing offers the possibility of diagnosis, therapy and prevention of illnesses as well as the targeted modification of the human genome. Rapid sequencing methods are required to allow the use of this potential. Base sequencing of deoxyribonucleic acid (DNA) and ribonucleic acid (RNA) is one of the most important analytical techniques in biotechnology, the pharmaceutical industry, food industry, medical diagnostics and other fields of application.

There are many DNA sequencing methods available, such as the Sanger sequencing using dideoxy termination and denaturing gel electrophoresis (Sanger, F. et al., Proc. Natl. Acad. Sci. U.S.A. 75, 5463-5467 (1977)), Maxam-Gilbert sequencing using chemical cleavage and denaturing gel electrophoresis (Maxam, A. M. & Gilbert, W. Proc Natl Acad Sci USA 74, 560-564 (1977)), pyro-sequencing detection pyrophosphate (PPi) released during the DNA polymerase reaction (Ronaghi, M. et al., Science 281, 363, 365 (1998)), and sequencing by hybridization (SBH) using oligonucleotides (Lysov, I. et al., Dokl Akad Nauk SSSR 303, 1508-1511 (1988); Bains W. & Smith G. C. J. Theor Biol 135, 303-307(1988); Drnanac, R. et al., Genomics 4, 114-128 (1989); Khrapko, K. R. et al., FEBS Lett 256. 118-122 (1989); Pevzner P. A. J Biomol Struct Dyn 7, 63-73 (1989); Southern, E. M. et al., Genomics 13, 1008-1017 (1992)).

Ronaghi et al., (Anal. Biochem. 267, pp. 65-71 (1999)) referred to a method of sequencing both strands of a nucleic acid. The method involves PCR amplification of a template nucleic acid with a biotinylated primer and a non-biotinylated primer. The amplified product, comprising a biotinylated strand and a non-biotinylated strand is strand separated. The authors referred to the use of streptavidin coated bead for strand separation. The biotinylated strand remains attached to the bead while the non-biotinylated strand is separated from the bead under denaturing conditions. The two strands (biotinylated and non-biotinylated) are sequenced separately. Unlike the present invention which uses solid-phase sequencing for both strands, this method uses solid-phase sequencing for the biotinylated strand and solution phase sequencing for the non-biotinylated strand. Hence, Ronaghi's method is similar to the traditional method of DNA sequencing comprising strand separation (e.g., using a urea gel) of a template before sequencing. Thus, Ronaghi's method suffers from the same disadvantage as the traditional methods; requirement of a labor intensive step of strand separation and isolation of individual strands prior to sequencing. The disadvantages of Ronaghi's method increases geometrically as the number of parallel sequencing reactions increase. For example, the parallel sequencing of 1000 double stranded templates would require 1000 separations and 2000 single strand isolations. Furthermore, Ronaghi's method, like all methods based on strand separation, is limited to the determination of sequences from two primers (one for each strand) per double strand template.

Sequencing based on chemical cleavage has proven to be difficult to automate. Other sequencing methods are labor intensive due to the need to perform a hybridization step for every sequencing effort. In many situations, the hybridization step is the rate-limiting step in a sequencing reaction.

Attempts have been made for sequencing from two ends of a nucleic acid using, for example, two distinctly labeled sequencing primers (e.g., Li-Cor of Lincoln, Nebraska) in a Sanger sequencing reaction (Sanger, F. et al., Proc. Natl. Acad. Sci. U.S.A. 75, 5463-5467 (1977). These methods are variations of manual sequencing and require a size fractionation (e.g., a gel) step to determine a sequence. While size fractionation may be suitable for small sample sizes, genomic sequencing using size fractionation techniques would require 1,500,000 size fractionation gels (assuming an optimistic capability of 2000 bp per gel). For these reasons, sequencing methods involving size fractionation have not been adapted to sequencing of human genomes.

SUMMARY OF THE INVENTION

The present invention provides for a method of sequencing a nucleic acid from multiple primers with a single primer hybridization step. In this method, two or more sequencing primers are hybridized to the template DNA to be sequenced. The template DNA may be single stranded or denatured double stranded. All the sequencing primers are then blocked except for one. Sequencing (e.g., pyrophosphate sequencing) is performed again by elongating the unblocked primer. The elongation is either allowed to go to completion (with additional polymerase and dNTPs if necessary) or is terminated (by polymerase, ddNTPs and optionally dNTPs); in either situation, preventing further elongation of the unblocked primer. Chain completion and/or termination reagents are removed. Then one of the blocked primers is unblocked and sequencing is performed by elongating the newly unblocked primer. This process is continued until all the sequencing primers are deblocked and sequenced. In a preferred embodiment, two primers (one blocked and one unblocked) are used to sequence both ends of a double stranded nucleic acid.

BRIEF DESCRIPTION OF THE DRAWINGS

FIG. 9 illustrates the results of sequencing a *Staphylococcus aureus* genome.

FIG. 10 illustrates the average read lengths in one experiment involving double ended sequencing.

FIG. 11 illustrates the number of wells for each genome span in a double ended sequencing experiment.

FIG. 12 illustrates a typical output and alignment string from a double ended sequencing procedure. Sequences shown in order, from top to bottom: SEQ ID NO:9-SEQ ID NO:22.

DETAILED DESCRIPTION OF INVENTION

Figure 1A:
FIG. 1 illustrates an exemplary double ended sequencing process

Traditionally, the sequencing of two ends of a double stranded DNA molecule would require at the very least the hybridization of primer, sequencing of one end, hybridization of a second primer, and sequencing of the other end. The alternative method is to separate the individual strands of the double stranded nucleic acid and individually sequence each strand. The present invention provides a third alternative that is more rapid and less labor intensive than the first two methods.

The present invention provides for a method of sequential sequencing of nucleic acids from multiple primers. References to DNA sequencing in this application are directed to sequencing using a polymerase wherein the sequence is determined as the nucleotide triphosphate (NTP) is incorporated into the growing chain of a sequencing primer. One example of this type of sequencing is the pyro-sequencing detection pyrophosphate method (see, e.g., U.S. Pat. Nos. 6,274,320, 6258,568 and 6,210,891, each of which is incorporated in total herein by reference.).

In one embodiment, the present invention provides for a method for sequencing two ends of a template double stranded nucleic acid. The double stranded DNA is comprised of two single stranded DNA; referred to herein as a first single stranded DNA and a second single stranded DNA. A first primer is hybridized to the first single stranded DNA and a second primer is hybridized to the second single stranded DNA. The first primer is unblocked while the second primer is blocked.

The terms "blocked" or "blocked primer" is defined in this disclosure any primer that is prevented from elongation by a polymerase. Blockage may be a chemical blocking group that prevents a primer from polymerization by DNA polymerase. Further, the chemical group blocking should be reversible so that after reversion, the oligonucleotide is once again able to serve as a sequencing primer. Thus, blockage means the same as blocking, blocked means the same as protected, deblocked means the same as deblocking.

"Protection," "protected," blockage" and "blocking" are defined in this disclosure as being the addition of a chemical group to reactive sites on the primer that prevents a primer from polymerization by DNA polymerase. Further, the addition of such chemical protecting groups should be reversible so that after reversion, the now deprotected primer is once again able to serve as a sequencing primer. The nucleic acid sequence is determined in one direction (e.g., from one end of the template) by elongating the first primer with DNA polymerase using conventional methods such as pyrophosphate sequencing. The second primer is then deprotected, and the sequence is determined by elongating the second primer in the other direction (e.g., from the other end of the template) using DNA polymerase and conventional methods such as pyrophosphate sequencing. The sequences of the first and second primers are specifically designed to hybridize to the two ends of the double stranded DNA or at any location along the template in this method.

In addition to the definition above, protection and blockage may also be extrinsic to the primer. For example, an antibody or other protein may bind a downstream site (e.g. sequence specific DNA binding protein) to create a blocked primer even though the primer is not chemically different from an unblocked primer. For example, blockage and protection may be mediated by a DNA binding protein that binds downstream from a nucleic acid primer and prevents elongation. In this case, the primer is considered blocked or protected. Furthermore, if the DNA binding protein is removable, the primer is considered to be reversibly blocked or reversibly protected. A DNA binding protein is any synthetic or natural DNA binding protein or functional equivalents thereof.

In another embodiment, the present invention provides for a method of sequencing a nucleic acid from multiple primers. In this method a number of sequencing primers are hybridized to the template nucleic acid to be sequenced. All the sequencing primers are reversibly blocked except for one. A blocked primer is an oligonucleotide primer that cannot be extended with polymerase and dNTPs which are commonly used in DNA sequencing reactions. A reversibly blocked primer is a blocked primer which can be deblocked. All blocked primers referred to in this invention are reversibly blocked. After deblocking, a reversibly blocked primer functions as a normal sequencing primer and is capable of participating in a normal sequencing reaction.

The present invention provides for a method of sequential sequencing a nucleic acid from multiple primers. The method comprises the following steps: First, one or more template nucleic acids to be sequenced are provided. Second, a plurality of sequencing primers is hybridized to the template nucleic acid or acids. The number of sequencing primers may be represented by the number n where n can be any positive number greater than 1. That number may be, for example, 2, 3, 4, 5, 6, 7, 8, 9, 10, or greater. Of the primers, n-1 number may be blocked by a blocking group. So, for example, if n is 2, 3, 4, 5, 6, 7, 8, 9, or 10, n-1 would be 1, 2, 3, 4, 5, 6, 7, 8, and 9 respectively. The remaining primer (e.g., n number primers—(n-1) number of blocked primers=one remaining primer) is unblocked. Third, the unblocked primer is extended and the template DNA sequence is determined by conventional methods such as, for example, pyrophosphate sequencing. Fourth, after the sequencing of the first primer, one of the remaining blocked primers is unblocked. Fifth, unblocked primer is extended and the template DNA sequence is determined by conventional methods such as, for example, pyrophosphate sequencing. Optionally, the method may be repeated until sequencing is performed on all the blocked primers.

In another aspect, the present invention includes a method of sequential sequencing of a nucleic acid comprising the steps of: (a) hybridizing 2 or more sequencing primers to the nucleic acid wherein all the primers except for one are reversibly blocked; (b) determining a sequence of one strand of the nucleic acid by polymerase elongation from the unblocked primer; (c) deblocking one of the reversibly blocked primers into an unblocked primer; (d) repeating steps (b) and (c) until all the reversibly blocked primers are deblocked and used for determining a sequence. In one embodiment, this method comprises one additional step between steps (b) and (c), i.e., the step of terminating the elongation of the unblocked primer by contacting the unblocked primer with DNA polymerase and one or more of a nucleotide triphosphate or a dideoxy nucleotide triphosphate. In yet another embodiment, this method further comprises an additional step between said step (b) and (c), i.e., terminating the elongation of the unblocked primer by contacting the unblocked primer with DNA polymerase and a dideoxy nucleotide triphosphate from ddATP, ddTTP, ddCTP, ddGTP or a combination thereof.

In another aspect, this invention includes a method of sequencing a nucleic acid comprising: (a) hybridizing a first unblocked primer to a first strand of the nucleic acid; (b) hybridizing a second blocked primer to a second strand; (c) exposing the first and second strands to polymerase, such that the first unblocked primer is extended along the first strand; (d) preventing further elongation of the first sequencing primer (also referred to as completing the extension of the first sequencing primer); (e) deblocking the second sequencing primer; and (f) exposing the first and second strands to polymerase so that the second sequencing primer is extended along the second strand. The preventing further elongation (i.e., completing elongation) may be accomplished by any suitable means including allowing primer runoff or primer capping (e.g., with ddNTPs or by chemical means). In a preferred embodiment, preventing further elongation or completing comprises capping or terminating the elongation.

In another embodiment, the present invention provides for a method for sequencing two ends of a template double stranded nucleic acid that comprises a first and a second single stranded DNA. In this embodiment, a first primer is hybridized to the first single stranded DNA and a second primer is hybridized to the second single stranded DNA in the same step. The first primer is unblocked while the second primer is blocked. Following hybridization, the nucleic acid sequence is determined in one direction (e.g., from one end of the template) by elongating the first primer with DNA polymerase using conventional methods such as pyrophosphate sequencing. In a preferred embodiment, the polymerase is devoid of 3' to 5' exonuclease activity. The second primer is then deblocked, and its sequence is determined by elongating the second primer in the other direction (e.g., from the other end of the template) with DNA polymerase using conventional methods such as pyrophosphate sequencing. As described earlier, the sequences of the first primer and the second primer are designed to hybridize to the two ends of the double stranded DNA or at any location along the template. This technique is especially useful for the sequencing of many template DNAs that contain unique sequencing primer hybridization sites on its two ends. For example, many cloning vectors provide unique sequencing primer hybridization sites flanking the insert site to facilitate subsequent sequencing of any cloned sequence (e.g., Bluescript, Stratagene, La Jolla, Calif.).

One benefit of this method of the present invention is that both primers may be hybridized in a single step. The benefits of this and other methods are especially useful in parallel sequencing systems where hybridizations are more involved than normal. Examples of parallel sequencing systems are disclosed in copending U.S. patent application Ser. No. 10/104,280, the disclosure of which is incorporated in total herein.

The oligonucleotide primers of the present invention may be synthesized by conventional technology, e.g., with a commercial oligonucleotide synthesizer and/or by ligating together subfragments that have been so synthesized.

In another embodiment of the invention, the length of the double stranded target nucleic acid may be determined. Methods of determining the length of a double stranded nucleic acid are known in the art. The length determination may be performed before or after the nucleic acid is sequenced. Known methods of nucleic acid molecule length determination include gel electrophoresis, pulsed field gel electrophoresis, mass spectroscopy and the like. Since a blunt ended double stranded nucleic acid is comprised of two single strands of identical lengths, the determination of the length of one strand of a nucleic acid is sufficient to determine the length of the corresponding double strand.

The sequence reaction according to the present invention also allows a determination of the template nucleic acid length. First, a complete sequence from one end of the nucleic acid to another end will allow the length to be determined. Second, the sequence determination of the two ends may overlap in the middle allowing the two sequences to be linked. The complete sequence may be determined and the length may be revealed. For example, if the template is 100 bps long, sequencing from one end may determine bases 1 to 75; sequencing from the other end may determine bases 25 to 100; there is thus a 51 base overlap in the middle from base 25 to base 75; and from this information, the complete sequence from 1 to 100 may be determined and the length, of 100 bases, may be revealed by the complete sequence.

Another method of the present invention is directed to a method comprising the following steps. First a plurality of sequencing primers, each with a different sequence, is hybridized to a DNA to be sequenced. The number of sequencing primers may be any value greater than one such as, for example, 2, 3, 4, 5, 6, 7, 8, 9, 10 or more. All of these primers are reversibly blocked except for one. The one unblocked primer is elongated in a sequencing reaction and a sequence is determined. Usually, when a primer is completely elongated, it cannot extend and will not affect subsequent sequencing from another primer. If desired, the sequenced primer may be terminated using excess polymerase and dNTP or using ddNTPs. If a termination step is taken, the termination reagents (dNTPs and ddNTPs) should be removed after the step. Then, one of the reversibly blocked primers is unblocked and sequencing from the second primer proceeds. The steps of deblocking a primer, sequencing from the deblocked primer, and optionally, terminating sequencing from the primer is repeated until all the blocked primers are unblocked and used in sequencing.

The reversibly blocked primers should be blocked with different chemical groups. By choosing the appropriate method of deblocking, one primer may be deblocked without affecting the blocking groups of the other primers. In a preferred embodiment, the blocking group is $PO_4$. That is, the second primer is blocked by $PO_4$ and deblocking is accomplished by T4 polynucleotide kinase (utilizing its 3'-phosphatase activity) or calf-intestinal alkaline phosphatase (CIAP) or any suitable phosphatase. In another preferred embodiment, the blocking is a thio group or a phosphorothiol group.

The template nucleic acid may be a DNA, RNA, or peptide nucleic acid (PNA). While DNA is the preferred template, RNA and PNA may be converted to DNA by known techniques such as random primed PCR, reverse transcription, RT-PCR, or a combination of these techniques. Further, the methods of the invention are useful for sequencing nucleic acids of unknown and known sequence. The sequencing of nucleic acid of known sequence would be useful, for example, for confirming the sequence of synthesized DNA or for confirming the identity of suspected pathogen with a known nucleic acid sequence. The nucleic acids may be a mixture of more than one population of nucleic acids. It is known that a sequencing primer with sufficient specificity (e.g., 20 bases, 25 bases, 30 bases, 35 bases, 40 bases, 45 bases, or 50 bases) may be used to sequence a subset of sequences in a long nucleic acid or in a population of unrelated nucleic acids. Thus, for example, the template may be one sequence of 10 Kb or ten sequences of 1 Kb each. In a preferred embodiment, the template DNA is between 50 bp to 700 bp in length. The DNA can be single stranded or double stranded.

In the case where the template nucleic acid is single stranded, a number of primers may be hybridized to the template nucleic acid as shown below:

5'—primer 4—3' 5'—primer 3—3' 5'—primer 2—3'
    5'—primer 1—3'
3'—template nucleic acid—5'

In this case, it is preferred that the initial unblocked primer would be the primer that hybridizes at the most 5' end of the template. See primer 1 in the above illustration. In this orientation, the elongation of primer 1 would not displace (by strand displacement) primer 2, 3, or 4. When sequencing from primer 1 is finished, primer 2 can be unblocked and nucleic acid sequencing can commence. The sequencing from primer 2 may displace primer 1 or the elongated version of primer one but would have no effect on the remaining blocked primers (primers 3 and 4). Using this order, each primer may be used sequentially and a sequencing reaction from one primer would not affect the sequencing from a subsequent primer.

One feature of the invention is the ability to use multiple sequencing primers on one or more nucleic acids and the ability to sequence from multiple primers using only one hybridization step. In the hybridization step, all the sequencing primers (e.g. the n number of sequencing primers) may be hybridized to the template nucleic acid(s) at the same time. In conventional sequencing, usually one hybridization step is required for sequencing from one primer. One feature of the invention is that the sequencing from n primers (as defined above) may be performed by a single hybridization step. This effectively eliminates n-1 hybridization step.

In a preferred embodiment, the sequences of the n number of primers are sufficiently different that the primers do not cross hybridize or self-hybridize. Cross hybridization refers to the hybridization of one primer to another primer because of sequence complementarity. One form of cross hybridization is commonly referred to as a "primer dimer." In the case of a primer dimer, the 3' ends of two primers are complementary and form a structure that when elongated, is approximately the sum of the length of the two primers. Self-hybridization refers to the situation where the 5' end of a primer is complementary to the 3' end of the primer. In that case, the primer has a tendency to self hybridize to form a hairpin-like structure.

A primer can interact or become associated specifically with the template molecule. By the terms "interact" or "associate", it is meant herein that two substances or compounds (e.g., primer and template; chemical moiety and nucleotide) are bound (e.g., attached, bound, hybridized, joined, annealed, covalently linked, or otherwise associated) to one another sufficiently that the intended assay can be conducted. By the terms "specific" or "specifically", it is meant herein that two components bind selectively to each other. The parameters required to achieve specific interactions can be determined routinely, e.g., using conventional methods in the art.

To gain more sensitivity or to help in the analysis of complex mixtures, the blocked primers can be modified (e.g., derivatized) with chemical moieties designed to give clear unique signals. For example, each blocked primer can be derivatized with a different natural or synthetic amino acid attached through an amide bond to the oligonucleotide strand at one or more positions along the hybridizing portion of the strand. The chemical modification can be detected, of course, either after having been cleaved from the target nucleic acid, or while in association with the target nucleic acid. By allowing each blocked target nucleic acid to be identified in a distinguishable manner, it is possible to assay (e.g., to screen) for a large number of different target nucleic acids in a single assay. Many such assays can be performed rapidly and easily. Such an assay or set of assays can be conducted, therefore, with high throughput efficiency as defined herein.

In the methods of the invention, after a first primer is elongated and the sequence of the template DNA is determined, a second primer is deblocked and sequenced. There is no interference between the sequencing reaction of the first primer with the sequencing reaction of the second, now unblocked, primer because the first primer is completely elongated or terminated. Because the first primer is completely elongated, the sequencing from the second primer, using conventional methods such a pyrophosphate sequencing, will not be affected by the presence of the elongated first primer. The invention also provides a method of reducing any possible signal contamination from the first primer. Signal contamination refers to the incidences where the first primer is not completely elongated. In that case, the first primer will continue to elongate when a subsequent primer is deblocked and elongated. The elongation of both the first and second primers may interfere with the determination of DNA sequence.

In a preferred embodiment, the sequencing reaction (e.g., the chain elongation reaction) from one primer is first terminated or completed before a sequencing reaction is started on a second primer. A chain elongation reaction of DNA can be terminated by contacting the template DNA with DNA polymerase and dideoxy nucleotide triphosphates (ddNTPs) such as ddATP, ddTTP, ddGTP, and ddCTP. Following termination, the dideoxy nucleotide triphosphates may be removed by washing the reaction with a solution without ddNTPs. A second method of preventing further elongation of a primer is to add nucleotide triphosphates (dNTPs such as dATP, dTTP, dGTP and dCTP) and DNA polymerase to a reaction to completely extend any primer that is not completely extended. Following complete extension, the dNTPs and the polymerases are removed before the next primer is deblocked. By completing or terminating one primer before deblocking another primer, the signal to noise ratio of the sequencing reaction (e.g., pyrophosphate sequencing) can be improved. A third method may involve enzymes, proteins or other agents that can recognize a double strand region >25 bases and cut in the unextended portion of the single strand region.

The steps of (a) optionally terminating or completing the sequencing, (b) deblocking a new primer, and (c) sequencing from the deblocked primer may be repeated until a sequence is determined from the elongation of each primer. In this method, the hybridization step comprises "n" number of primers and one unblocked primer. The unblocked primer is sequenced first and the steps of (a), (b) and (c) above may be repeated.

In a preferred embodiment, pyrophosphate sequencing is used for all sequencing conducted in accordance with the method of the present invention.

Figure 1B:
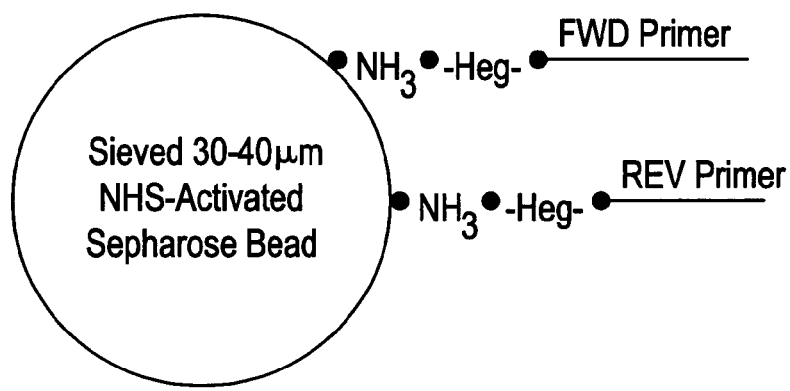
Figure 2:
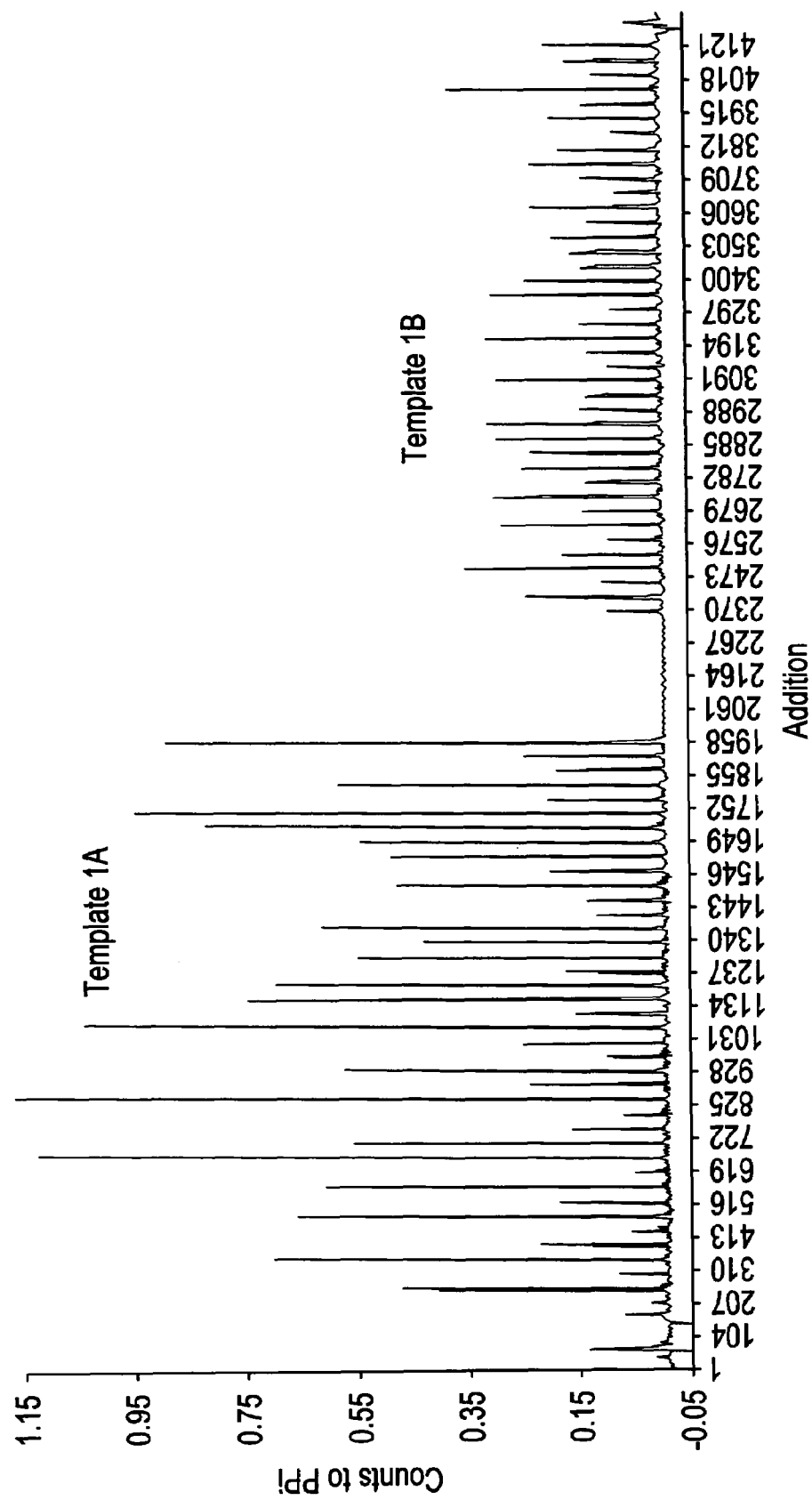
FIG. 2 illustrates the results of Double-Ended Sequencing demonstration on a pyrosequencing apparatus from 454 Corp.
Figure 3:
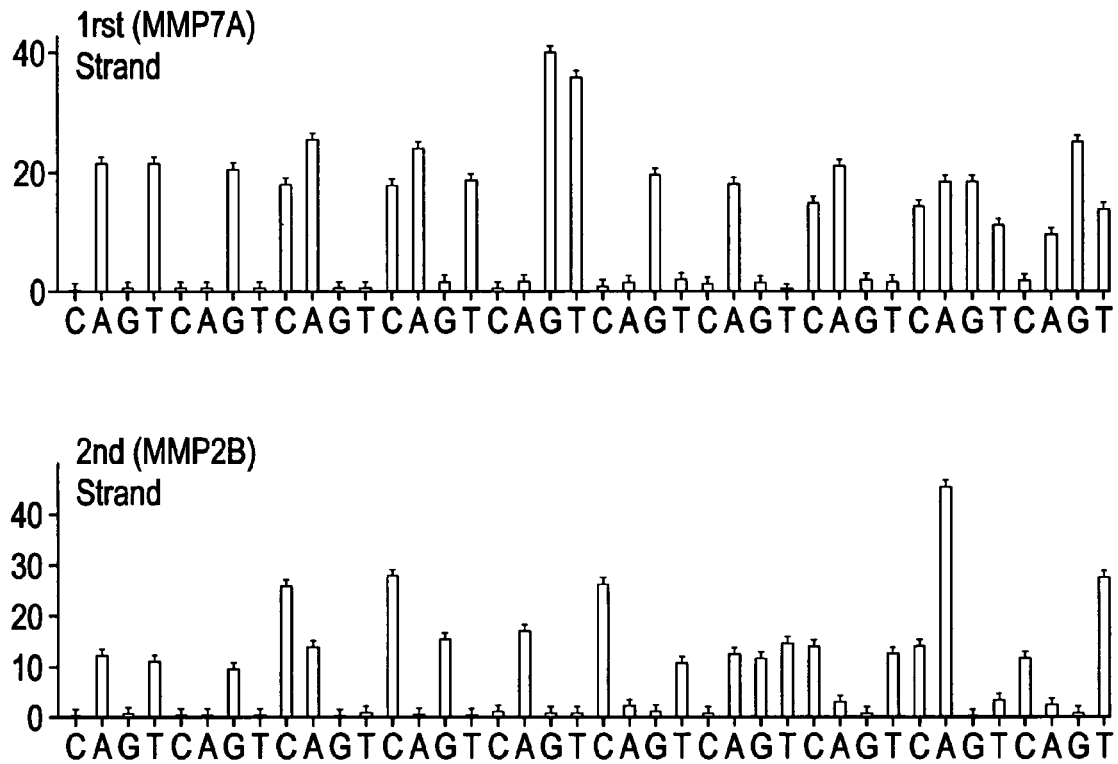
FIG. 3 illustrates the analysis Double-Ended Sequencing results showing that the sequence of both ends of a DNA template are determined. SEQ ID NO:6: atgcacatggttgacacagtggt; SEQ ID NO:7: atgcacatggttgacacagtgg; SEQ ID NO:8: atgccaccgacctagtctcaaactt.

In another preferred embodiment, the double ended sequencing is performed according to the process outlined in FIG. 1. This process may be divided into six steps: (1) creation of a capture bead (FIGS. 1A and B); (2) emulsion PCR amplification (FIG. 1C); (3) hybridization of blocked and unblocked primers (FIG. 1D); (4) sequencing of the first strand by extension of the unblocked primer (e.g., pyrophosphate sequencing) (FIG. 1E); (4A) optional termination/completion of sequencing from the first strand (FIG. 1E) followed by removal of the termination/completion reagents (FIG. 1F); (5) preparation of the second strand by deblocking a previously blocked primer (FIG. 3H); (6) sequencing of the second strand by addition of polymerase (FIG. 3I) and sequencing by elongation of the unblocked primer (FIG. 1J). The data that is collected from sequencing both strands is shown in FIG. 2. This data is further analyzed to yield sequence data in FIG. 3.

Figure 4:
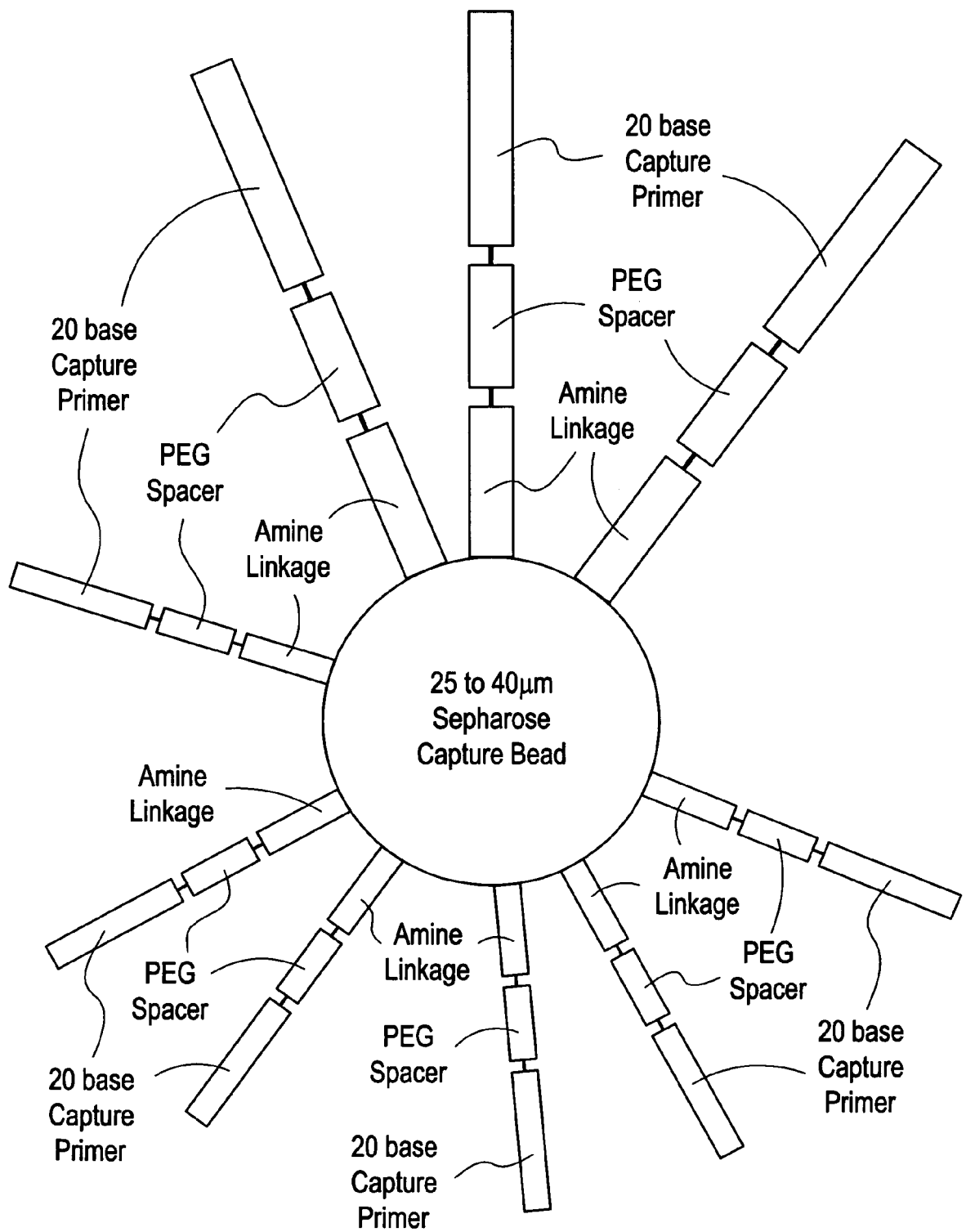
FIG. 4 illustrates an exemplary DNA capture bead.

In step 1, an N-hydroxysuccinimide (NHS)-activated capture bead (e.g., Amersham Biosciences, Piscataway, N.J.) (FIG. 1A, FIG. 4) is coupled to two different primers via a 5'-amine labeled group. The two primers correspond to the 5'-end of the sense (forward capture primer) and the antisense (reverse capture primer) strand of the template to be amplified. (FIG. 1B). This would result in a bead with both capture primers in the 5'-3' orientation. These primers are 40-mers and consist of two parts-a 20 base PCR primer linked to a 20 base sequencing primer. The 20-mer PCR primers are utilized for PCR amplification and the 20-mer sequencing primers are utilized to derive sequence information from DNA molecules extended from the DNA capture primers. NHS coupling forms a chemically stable amide bond with ligands containing primary amino groups. In addition, biotin may be coupled to the capture bead as well using amine-labeled biotin. The biotin group provides a useful mechanism for binding additional sequencing reagents (e.g., pyrophosphate sequencing reagents) to the bead. The beads (i.e., solid nucleic acid capturing supports) used herein may be of any convenient size and fabricated from any number of known materials. Example of such materials include: inorganics, natural polymers, and synthetic polymers. Specific examples of these materials include: cellulose, cellulose derivatives, acrylic resins, glass; silica gels, polystyrene, gelatin, polyvinyl pyrrolidone, co-polymers of vinyl and acrylamide, polystyrene cross-linked with divinylbenzene or the like (see, Merrifield Biochemistry 1964, 3, 1385-1390), polyacrylamides, latex gels, polystyrene, dextran, rubber, silicon, plastics, nitrocellulose, celluloses, natural sponges, silica gels, glass, metals plastic, cellulose, cross-linked dextrans (e.g., Sephadex™) and agarose gel (Sepharose™) and solid phase supports known to those of skill in the art. In a preferred embodiment, the capture beads are Sepharose beads approximately 25 to 30 μM in diameter.

The nucleic acid template may be attached to the capture bead in any manner known in the art. Numerous methods exist in the art for attaching the DNA to a microscopic bead. Covalent chemical attachment of the DNA to the bead can be accomplished by using standard coupling agents, such as water-soluble carbodiimide, to link the 5'-phosphate on the DNA to amine-coated microspheres through a phosphoamidate bond. Another alternative is to first couple specific oligonucleotide linkers to the bead using similar chemistry, and to then use DNA ligase to link the DNA to the linker on the bead. Other linkage chemistries include the use of N-hydroxysuccinamide (NHS) and its derivatives, to join the oligonucleotide to the beads. In such a method, one end of the oligonucleotide may contain a reactive group (such as an amide group) which forms a covalent bond with the solid support, while the other end of the linker contains another reactive group which can bond with the oligonucleotide to be immobilized. In a preferred embodiment, the oligonucleotide is bound to the DNA capture bead by covalent linkage. However, non-covalent linkages, such as chelation or antigen-antibody complexes, may be used to join the oligonucleotide to the bead.

Oligonucleotide linkers can be employed which specifically hybridize to unique sequences at the end of the DNA fragment, such as the overlapping end from a restriction enzyme site or the "sticky ends" of bacteriophage lambda based cloning vectors, but blunt-end ligations can also be used beneficially. These methods are described in detail in U.S. Pat. No. 5,674,743, the disclosure of which is incorporated in toto herein. It is preferred that any method used to immobilize the beads will continue to bind the immobilized oligonucleotide throughout the steps in the methods of the invention. In a preferred embodiment, the oligonucleotide is bound to the DNA capture bead by covalent linkage. However, non-covalent linkages, such as chelation or antigen-antibody complexes, may be used to join the oligonucleotide to the bead.

Figure 1C:
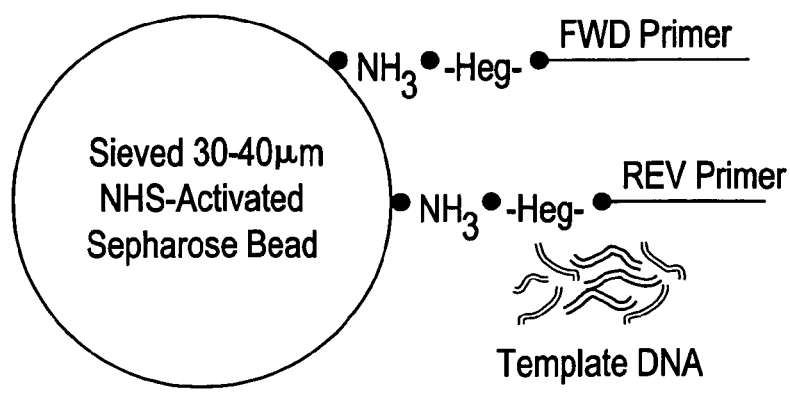

In step 2, template DNA which has the forward and reverse primers as adapters is added, and the DNA is amplified through a PCR amplification strategy (FIG. 1C). In one embodiment, the template DNA has a DNA adaptor ligated to both the 5' and 3' end. Adaptors are 40-mers that contain the sequences for PCR amplification and sequencing in tandem as one unit. Two different adaptors are linked to the ends of a DNA template as part of the Sample Preparation process. In one embodiment, the DNA is amplified by Emulsion Polymerase Chain Reaction, Drive to Bead Polymerase Chain Reaction, Rolling Circle Amplification, or Loop-mediated Isothermal Amplification. In a preferred embodiment, the template DNA with adapters is added such that one strand of DNA molecule would hybridize with one of the primers on the DNA capture bead (contains millions of forward and reverse capture primers in the 5'-3' orientation). The DNA capture beads are then resuspended in a PCR reaction mixes, containing the forward and reverse primers, emulsified and then amplified. The amplification reaction also consists of two steps: a) solution phase PCR amplification primers that help amplify the DNA template from a single molecule b) drive to bead step to capture the amplified DNA molecules to the bead. In all situations, the captured strand serves as a template for extension of the capture primer. As the capture primers are covalently attached to the beads, the capture-primer extended strand is also covalently attached to the beads. An important aspect of this process is the orientation of the two strands. The two capture primers contain sequences that correspond to the forward and reverse primers. Since the two capture primers can anneal to two separate, but complementary strands of the DNA, the capture beads will contain both strands of template DNA. Also since the capture primers are immobilized at the 5' end, the two strands will be immobilized in the 5'-3' direction. After amplification each capture primer contains an immobilized strand and a complementary strand. The beads are then pooled and alkali-treated to release the non-immobilized strand. The beads now contain a single-strand template which is ready for sequencing.

Figure 1D:
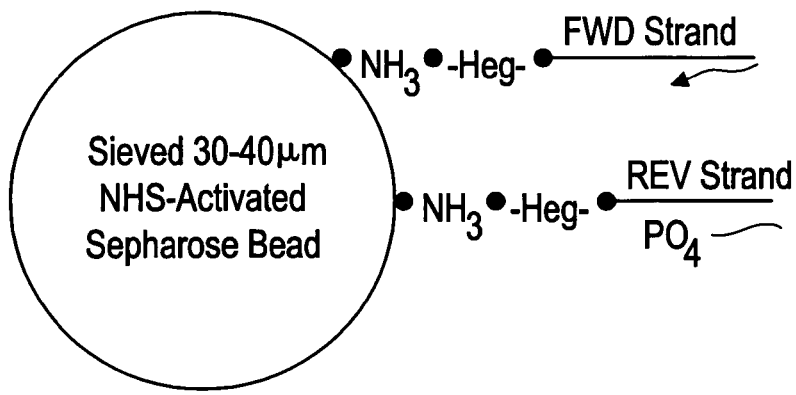

In step 3 sequencing enzymes and reagents are added to the reaction to facilitate sequencing by elongation of the primer (FIG. 1D). In a preferred embodiment, sulfurylase and luciferase (pyrophosphate sequencing enzymes) are supplied either in a separate bead-immobilized form or coupled to the DNA bead via biotin-streptavidin interaction. The addition of auxiliary enzymes during a sequencing method has been disclosed in U.S. Ser. No. 10/104,280 and U.S. Ser. No. 10/127,906, which are incorporated herein in their entireties by reference.

Figure 1E:
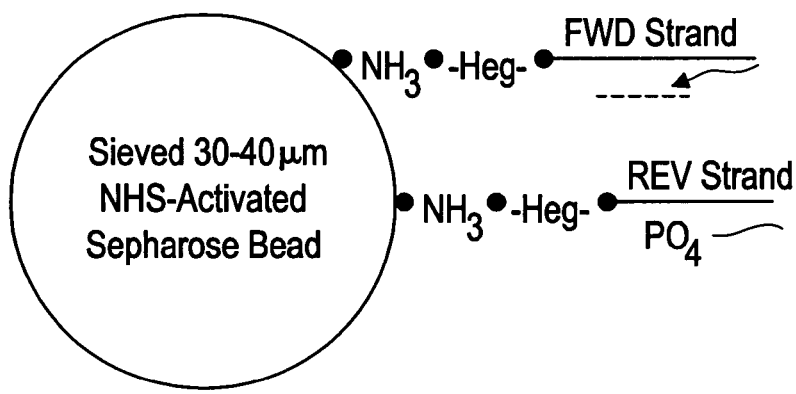

In step 4, the first strand of DNA is sequenced by elongating an unblocked primer. The sequencing method may be any method known to one of ordinary skill in the art (e.g., pyrophosphate sequencing) (FIG. 1E). In a preferred embodiment, the capture beads are loaded onto a PicoTiter plate (PTP) and sequenced automatically by pyrophosphate sequencing. In some cases, the nucleic acid sequence to be determined is close to the end of a template DNA. In that case, the elongation of the sequencing primer will terminate naturally as the polymerase reach the end of the DNA. In the majority of cases, the sequencing primer is not close to an end of the template DNA and after sufficient information is determined from the sequencing reaction, sequencing is terminated by completion or termination of the sequencing reaction.

Figure 1F:
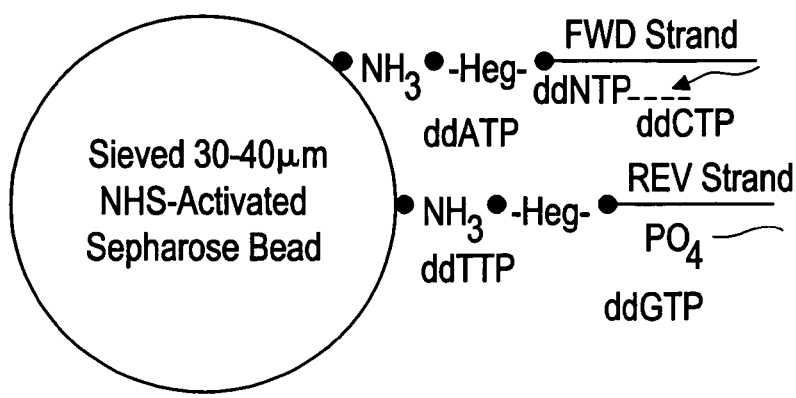
Figure 1G:
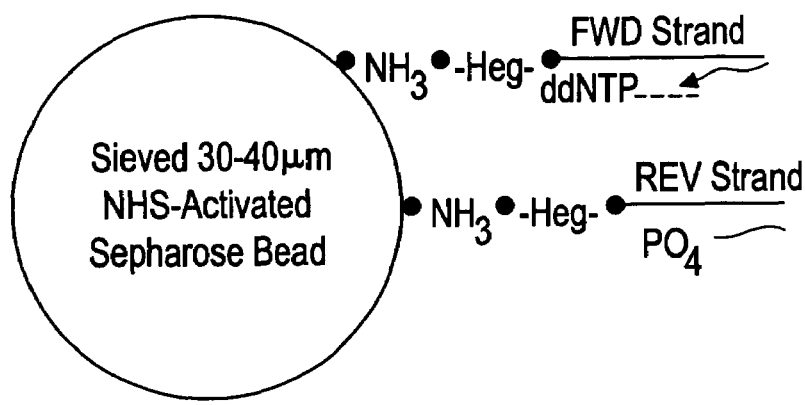
Figure 1H:
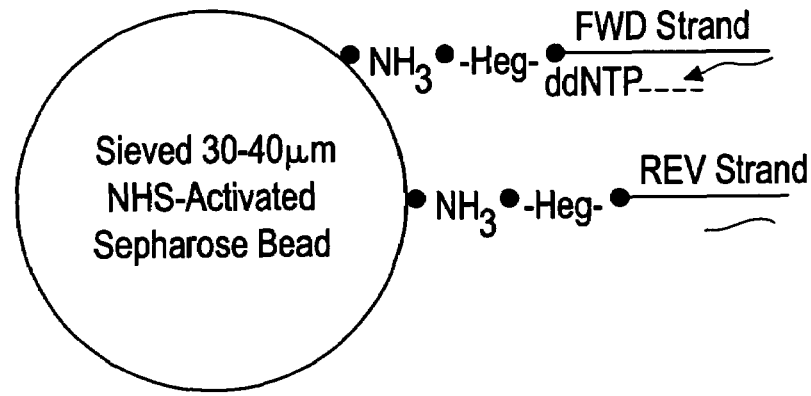
Figure 1I:
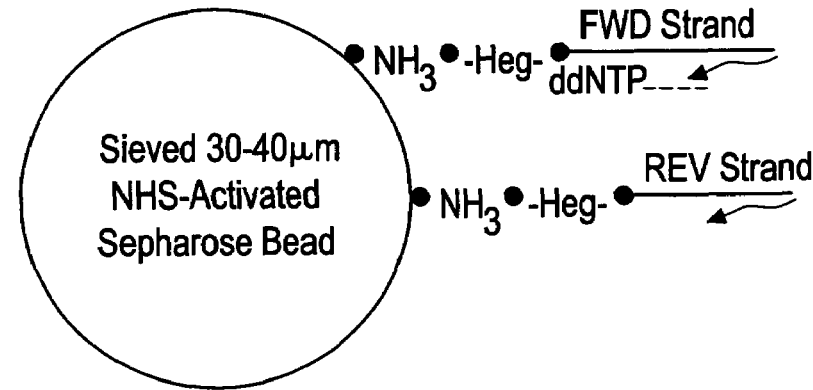

FIG. 1F shows one preferred method for terminating the sequencing reaction by the addition of ddNTP to the reaction. In step 5, the second strand of nucleic acid is prepared by adding apyrase to remove the ddNTPs (FIG. 1G) and polynucleotide kinase (PNK) or calf intestinal alkaline phosphatase or other enzymes that can remove the 3' phosphate group from the blocked primer strand (FIG. 1H).

Figure 1J:
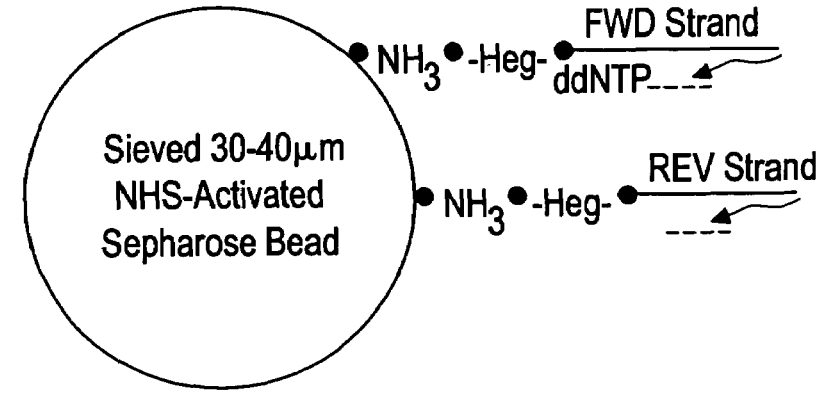

In step 6, polymerase is then added to prime the second strand (FIG. 1I) followed by sequencing of the second strand according to a standard method known to one of ordinary skill in the art (FIG. 1J). In step 7, the sequence of the both the first and second strand is analyzed such that a contiguous DNA sequence is determined (FIG. 2).

The methods of the invention may be performed in any scale. For example, a single bead may be used for sequencing in a test tube. In a preferred embodiment, the methods of sequencing are performed in parallel by loading the beads into onto wafers. A wafer is defined as a substrate with positionally defined sites on which a plurality of beads may be immobilized for a sufficiently long period of time so that a sequencing reaction may be performed on a nucleic acid bound to the bead. A wafer would allow the parallel double stranded sequencing from a plurality of beads. The design of wafers (also called PicoTiter plates and FORA) has been disclosed in U.S. Ser. No. 60/443,471, U.S. Ser. No. 60/465,071, U.S. Ser. No.: 10/104,280, U.S. Ser. No. 09/814,338, U.S. Ser. No.: 09/664,197, and U.S. Pat. No. 6,274,320, issued on Aug. 14, 2001 which are incorporated by reference herein.

In one aspect, the invention encompasses a method of sequencing a nucleic acid molecule comprising the steps of: a) hybridizing two or more sequencing primers to one or a plurality of single strands of the nucleic acid molecule wherein all the primers except for one are reversibly blocked primers; b) incorporating at least one base onto the nucleic acid molecule by polymerase elongation from an unblocked primer; c) preventing further elongation of the unblocked primer; d) deblocking one of the reversibly blocked primers into an unblocked primer; and e) repeating steps (b) to (d) until at least one of the reversibly blocked primers are deblocked and used for determining a sequence.

For use with this method, step (c) of preventing further elongation can comprise: i) completing the elongation from the unblocked primer with polymerase and dNTPs; or ii) terminating the elongation with polymerase in a manganese containing buffer, dNTPs, and at least one ddNTP; or iii) terminating the elongation chemically. The method can further comprise the step of removing the polymerase, dNTPs, and ddNTPs before step (d).

In this method, at least one reversibly blocked primer can be blocked by a chemical moiety selected from the group consisting of a $PO_4$ group, a thio group, and a phosphorothiol group. In addition, at least one reversibly blocked primer can include a 3' mismatched end that can be deblocked by contacting the primer with an exonuclease. At least one reversibly blocked primer can include one or more noncomplementary bases that forms a loop and does not hybridize to the nucleic acid molecule, wherein the one or more bases is not at the 5' or 3' end of the reversibly blocked primer, and wherein the reversibly blocked primer comprises a dideoxy nucleotide at its 3' end. In addition, at least one reversibly blocked primer is unblocked by endonuclease digestion of the one or more noncomplementary bases forming a nick at the one or more noncomplementary base.

According to this method, step (b) can include polymerase elongation at the nick by a strand-displacing polymerase. In addition, at least one reversibly blocked primer may comprise a sequence of 5'-NUX-3' wherein N represents an oligonucleotide sequence of any length, U is uracil, and X is a dideoxy-nucleotide. The reversibly blocked primer may be unblocked by Uracil DNA glycosylase and AP endonuclease to generate an unblocked primer with an extendable 3' end. Alternatively, at least one reversibly blocked primer may comprise a sequence of 5'-NYZ-3' wherein N represents an oligonucleotide sequence of any length, Y is a modified nucleotide, and Z represents a single nucleotide base; and wherein the modified nucleotide can be deblocked by formamidopyrimidine (fapy)-DNA glycosylase. This modified base can be, e.g., 8-oxoguanine, 8-oxoadenine, fapy-guanine, methyl-fapy-guanine, fapy-adenine, aflatoxin $B_1$-fapy-guanine, 5-hydroxy cytosine and 5-hydroxy-uracil.

As examples, the nucleic acid molecule used with this method can be genomic DNA, cDNA, or episomal DNA, and can be 100 to 1000 bp in length. In addition, at least one strand of the nucleic acid molecule or the primers can be attached to a solid support. Preferably, at least one primer is immobilized on a solid support to form an immobilized primer and at least one strand is linked to a solid support by hybridization with the immobilized primer. The solid support can be a spherical mobile solid support. In some cases, at least one primer comprises a detectable label. In addition, at least one sequencing primer may be hybridized to a sense strand of the nucleic acid and at least one sequencing primer hybridizes to an antisense strand of the nucleic acid molecule in step (a).

In accordance with this method, the polymerase elongation can be between 1 and 250 bases. The method can be performed, for example, in a reaction vessel such as a test tube, a reaction chamber of a PicoTiter plate, a reaction chamber of an array, or a microencapsulated reaction chamber of a water-in-oil emulsion. The sequencing can be performed by pyrophosphate sequencing or Sanger sequencing. Preferably, the polymerase is devoid of 3' to 5' exonuclease activity. Preferably, the polymerase is devoid of 3' to 5' exonuclease activity. The deblocking step can entail contacting a reversibly blocked primer with an agent to remove a $PO_4$.group on the reversibly blocked primer. This agent can be, e.g., polynucleotide kinase or alkaline phosphatase. In one application, the method can be used to determine a first nucleic acid sequence proximate to one end of the nucleic acid molecule and a second nucleic acid sequence proximate to a second end of the nucleic acid molecule.

In another aspect, the invention encompasses a method of sequencing a nucleic acid molecule comprising: a) hybridizing a first unblocked sequencing primer to a first strand of the nucleic acid molecule; b) hybridizing a second blocked sequencing primer to a second strand of the nucleic acid molecule; c) incorporating at least one base onto the first strand by extending the first unblocked primer with a polymerase; d) preventing further elongation of the unblocked primer; e) deblocking the second sequencing primer; and f) incorporating at least one base onto the second strand by extending the second primer with a polymerase; wherein steps (a) and (b) are performed in any order or simultaneously.

With this method, step (d) can include: i) completing the elongation from the unblocked primer with polymerase and dNTPs; or b) terminating the elongation with polymerase in a manganese containing buffer, dNTPs, and at least one ddNTP; or c) terminating the elongation chemically. The method can further comprise a step of removing the polymerase, dNTPs, and ddNTPs after the preventing step. In various aspects, the second primer can be blocked by a chemical moiety such as a $PO_4$ group, a thio group, and a phosphorothiol group. The method can be used, e.g., to determine at least a first nucleic acid sequence proximal to a first end of the nucleic acid molecule and determines a second nucleic acid sequence proximal to a second end of the nucleic acid molecule.

The invention also encompasses a method of determining a molecular haplotype of a DNA sample at multiple loci comprising the steps of: a) hybridizing 2 or more sequencing primers adjacent to a plurality of loci in a DNA sample wherein all the primers except for one are reversibly blocked primers and wherein each locus contains a nucleic acid sequence that determines a haplotype; b) determining a haplotype at one locus by polymerase elongation from an unblocked primer; c) preventing further elongation of the unblocked primer; d) deblocking one of the reversibly blocked primers into an unblocked primer; e) repeating steps (b) to (d) until all the reversibly blocked primers are deblocked and used for determining a molecular haplotype.

In this method, step (c) of preventing further elongation can comprise: i) completing the elongation from the unblocked primer with polymerase and dNTPs; or ii) terminating the elongation with polymerase in a manganese containing buffer, dNTPs, and at least one ddNTP; or iii) terminating the elongation chemically. The method can further comprise the step of removing the polymerase, dNTPs, and ddNTPs after the preventing step.

Additionally, the invention encompasses a method of sequencing a nucleic acid molecule comprising the steps of: a) hybridizing a sequencing primer to one strand of the nucleic acid molecule; b) incorporating at least one base onto one strand of the nucleic acid by polymerase elongation from the sequencing primer; c) preventing further elongation of the primer; and d) repeating steps (a) to (c) on the same strand of nucleic acid or on a different strand of nucleic acid until a desired amount of sequence is determined.

For certain aspects, step (c) of this method comprises: i) completing the elongation from the unblocked primer with polymerase and dNTPs; or ii) terminating the elongation with polymerase in a manganese containing buffer, dNTPs, and at least one ddNTP; or iii) terminating the elongation chemically. In addition, the method can further comprise the step of removing the polymerase, dNTPs, and ddNTPs after the preventing step.

The invention further encompasses a method of sequencing a plurality of double stranded nucleic acid molecules comprising the steps of: a) for each of the double stranded molecules, separating two strands of each double stranded nucleic acid and attaching each of the two complementary strands to a single bead, to generate a plurality of beads in a single reactor, each bead with both strands of the nucleic acid molecule attached thereto; b) determining the identity of at least one base of one of the strands; and (c) determining the identity of at least one base of the complementary strand of the nucleic acid molecule.

EXAMPLES

Example 1

Template Quality Control

The success of the Emulsion PCR reaction, a first step in the methods of this invention, was found to be related to the quality of the single stranded template species. Accordingly, the quality of the template material was assessed with two separate quality controls before initiating the Emulsion PCR protocol. First, an aliquot of the single-stranded template was run on the 2100 BioAnalyzer (Agilent). An RNA Pico Chip was used to verify that the sample included a heterogeneous population of fragments, ranging in size from approximately 200 to 500 bases. Second, the library was quantitated using the RiboGreen fluorescence assay on a Bio-Tek FL600 plate fluorometer. Samples determined to have DNA concentrations below 5 ng/µl were deemed too dilute for use.

Example 2

DNA Capture Bead Synthesis

Figure 5A:
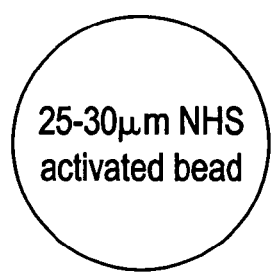
FIG. 5 illustrates the encapsulation of a bead comprising two oligonucleotide sequences for double stranded sequencing.
Figure 5B:
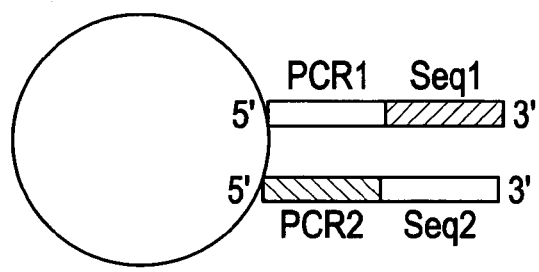
Figure 5C:
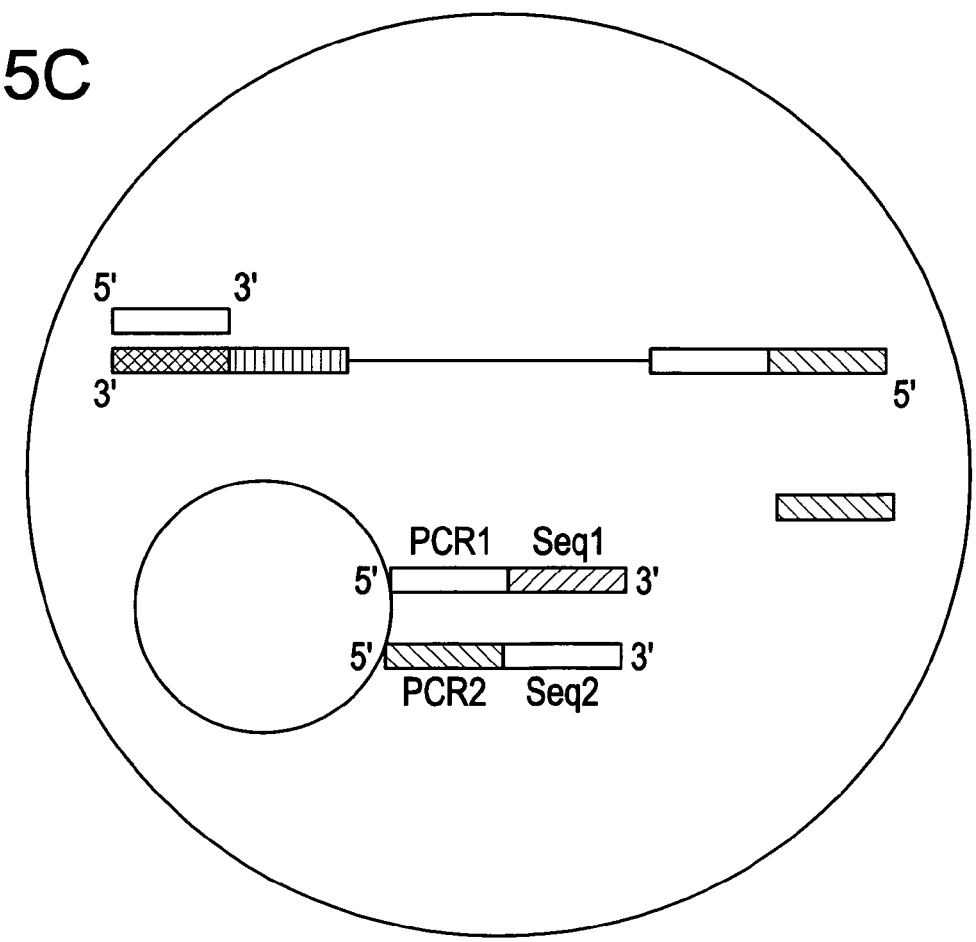

Packed beads from a 1 mL N-hydroxysuccinimide ester (NHS)-activated Sepharose HP affinity column (Amersham Biosciences, Piscataway, N.J.) were removed from the column. The 30-25 µm size beads were selected by serial passage through 30 and 25 µm pore filter mesh sections (Sefar America, Depew, N.Y., USA). Beads that passed through the first filter, but were retained by the second were collected and activated as described in the product literature (Amersham Pharmacia Protocol #71700600AP). Two different amine-labeled HEG (hexaethyleneglycol) long capture primers were obtained, corresponding to the 5' end of the sense and antisense strand of the template to be amplified, (5'-Amine-3 HEG spacers gcttacctgaccgacctctgcctatc-ccctgttgcgtgtc-3'; SEQ ID NO:23; and 5'-Amine-3 HEG spacers ccattccccagctcgtcttgccatctgttccctccctgtc-3'; SEQ ID NO:24) (IDT Technologies, Coralville, Iowa, USA). The primers were designed to capture of both strands of the amplification products to allow double ended sequencing, i.e., sequencing the first and second strands of the amplification products. The capture primers were dissolved in 20 mM phosphate buffer, pH 8.0, to obtain a final concentration of 1 mM. Three microliters of each primer were bound to the sieved 30-25 μm beads. See FIG. 5. The beads were then stored in a bead storage buffer (50 mM Tris, 0.02% Tween and 0.02% sodium azide, pH 8). The beads were quantitated with a hemacytometer (Hausser Scientific, Horsham, Pa., USA) and stored at 4° C. until needed.

Example 3

PCR Reaction Mix Preparation and Formulation

As with any single molecule amplification technique, contamination of the reactions with foreign or residual amplicon from other experiments could interfere with a sequencing run. To reduce the possibility of contamination, the PCR reaction mix was prepared in a in a UV-treated laminar flow hood located in a PCR clean room. For each 600,000 bead emulsion PCR reaction, the following reagents were mixed in a 1.5 ml tube: 225 μl of reaction mixture (1× Platinum HiFi Buffer (Invitrogen)), 1 mM dNTPs, 2.5 mM MgSO$_4$ (Invitrogen), 0.1% BSA, 0.01% Tween, 0.003 U/∞l thermostable PPi-ase (NEB), 0.125 μM forward primer (5'-gcttacctgaccgacctctg-3'; SEQ ID NO:1) and 0.125 μM reverse primer (5'-ccattccccagctcgtcttg-3'; SEQ ID NO:2) (IDT Technologies, Coralville, Iowa, USA) and 0.2 U/μl Platinum Hi-Fi Taq Polymerase (Invitrogen). Twenty-five microliters of the reaction mixture was removed and stored in an individual 200 μl PCR tube for use as a negative control. Both the reaction mixture and negative controls were stored on ice until needed.

Example 4

Binding Template Species to DNA Capture Beads

Successful clonal DNA amplification for sequencing relates to the delivery of a controlled number of template species to each bead. For the experiments described herein, the typical target template concentration was determined to be 0.5 template copies per capture bead. At this concentration, Poisson distribution dictates that 61% of the beads have no associated template, 30% have one species of template, and 9% have two or more template species. Delivery of excess species can result in the binding and subsequent amplification of a mixed population (2 or more species) on a single bead, preventing the generation of meaningful sequence data,. However, delivery of too few species will result in fewer wells containing template (one species per bead), reducing the extent of sequencing coverage. Consequently, it was deemed that the single-stranded library template concentration was important.

Template molecules were annealed to complimentary primers on the DNA capture beads by the following method, conducted in a UV-treated laminar flow hood. Six hundred thousand DNA capture beads suspended in bead storage buffer (see Example 9, above) were transferred to a 200 μl PCR tube. The tube was centrifuged in a benchtop mini centrifuge for 10 seconds, rotated 180°, and spun for an additional 10 seconds to ensure even pellet formation. The supernatant was removed, and the beads were washed with 200 μl of Annealing Buffer (20 mM Tris, pH 7.5 and 5 mM magnesium acetate). The tube was vortexed for 5 seconds to resuspend the beads, and the beads were pelleted as before. All but approximately 10 μl of the supernatant above the beads was removed, and an additional 200 μl of Annealing Buffer was added. The beads were again vortexed for 5 seconds, allowed to sit for 1 minute, and then pelleted as before. All but 10 μl of supernatant was discarded.

Next, 1.5 μl of 300,000 molecules/μl template library was added to the beads. The tube was vortexed for 5 seconds to mix the contents, and the templates were annealed to the beads in a controlled denaturation/annealing program preformed in an MJ thermocycler. The program allowed incubation for 5 minutes at 80° C., followed by a decrease by 0.1° C./sec to 70° C., incubation for 1 minute at 70° C., decrease by 0.1° C./sec to 60° C., hold at 60° C. for 1 minute, decrease by 0.1° C./sec to 50° C., hold at 50° C. for 1 minute, decrease by 0.1° C. /sec to 20° C., hold at 20° C. Following completion of the annealing process, the beads were removed from the thermocycler, centrifuged as before, and the Annealing Buffer was carefully decanted. The capture beads included on average 0.5 copy of single stranded template DNA bound to each bead, and were stored on ice until needed.

Example 5

Emulsification

The emulsification process creates a heat-stable water-in-oil emulsion containing 10,000 discrete PCR microreactors per microliter. This serves as a matrix for single molecule, clonal amplification of the individual molecules of the target library. The reaction mixture and DNA capture beads for a single reaction were emulsified in the following manner. In a UV-treated laminar flow hood, 200 μl of PCR solution (from Example 10) was added to the tube containing the 600,000 DNA capture beads (from Example 11). The beads were resuspended through repeated pipetting. After this, the PCR-bead mixture was incubated at room temperature for at least 2 minutes, allowing the beads to equilibrate with the PCR solution. At the same time, 450 μl of Emulsion Oil (4.5% (w:w) Span 80, 1% (w:w) Atlox 4912 (Uniqema, Del.) in light mineral oil (Sigma)) was aliquotted into a flat-topped 2 ml centrifuge tube (Dot Scientific) containing a sterile ¼ inch magnetic stir bar (Fischer). This tube was then placed in a custom-made plastic tube holding jig, which was then centered on a Fisher Isotemp digital stirring hotplate (Fisher Scientific) set to 450 RPM.

The PCR-bead solution was vortexed for 15 seconds to resuspend the beads. The solution was then drawn into a 1 ml disposable plastic syringe (Benton-Dickenson) affixed with a plastic safety syringe needle (Henry Schein). The syringe was placed into a syringe pump (Cole-Parmer) modified with an aluminum base unit orienting the pump vertically rather than horizontally. The tube with the emulsion oil was aligned on the stir plate so that it was centered below the plastic syringe needle and the magnetic stir bar was spinning properly. The syringe pump was set to dispense 0.6 ml at 5.5 ml/hr. The PCR-bead solution was added to the emulsion oil in a dropwise fashion. Care was taken to ensure that the droplets did not contact the side of the tube as they fell into the spinning oil.

Once the emulsion was formed, great care was taken to minimize agitation of the emulsion during both the emulsification process and the post-emulsification aliquotting steps. It was found that vortexing, rapid pipetting, or excessive mixing could cause the emulsion to break, destroying the discrete microreactors. In forming the emulsion, the two solutions turned into a homogeneous milky white mixture with the viscosity of mayonnaise. The contents of the syringe were emptied into the spinning oil. Then, the emulsion tube was removed from the holding jig, and gently flicked with a forefinger until any residual oil layer at the top of the emulsion disappeared. The tube was replaced in the holding jig, and stirred with the magnetic stir bar for an additional minute. The stir bar was removed from the emulsion by running a magnetic retrieval tool along the outside of the tube, and the stir bar was discarded.

Twenty microliters of the emulsion was taken from the middle of the tube using a P100 pipettor and placed on a microscope slide. The larger pipette tips were used to minimize shear forces. The emulsion was inspected at 50× magnification to ensure that it was comprised predominantly of single beads in 30 to 150 micron diameter microreactors of PCR solution in oil (schematic figure shown in FIG. 5). After visual examination, the emulsions were immediately amplified.

Example 6

Amplification

Figure 6:
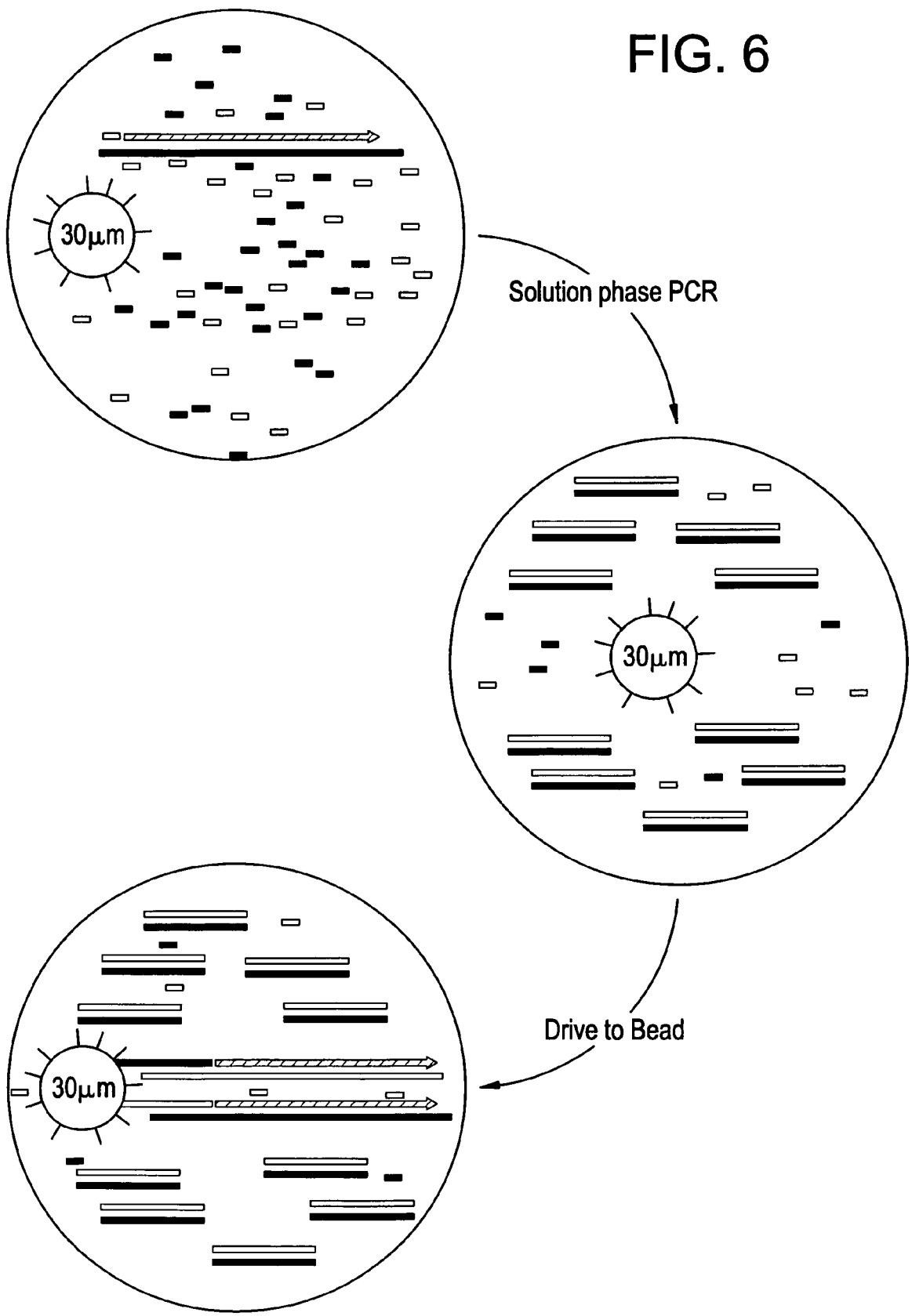
FIG. 6 illustrates solution phase PCR and drive to bead procedure—a step in a preferred embodiment of double ended sequencing.
Figure 7A:
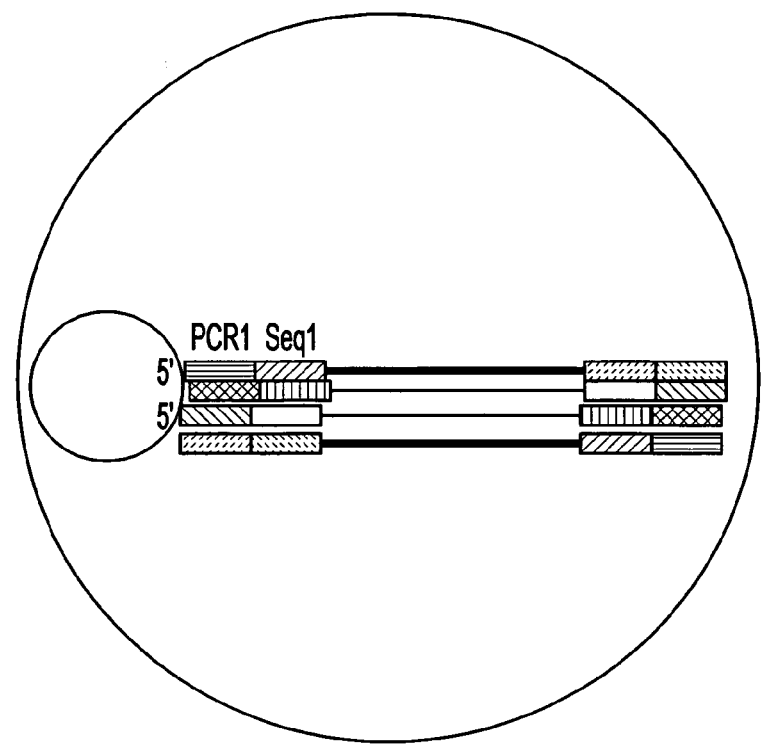
FIG. 7 illustrates emulsion breaking and recovery of amplified template DNA on a bead—a step in a preferred embodiment of double ended sequencing.
Figure 7B:
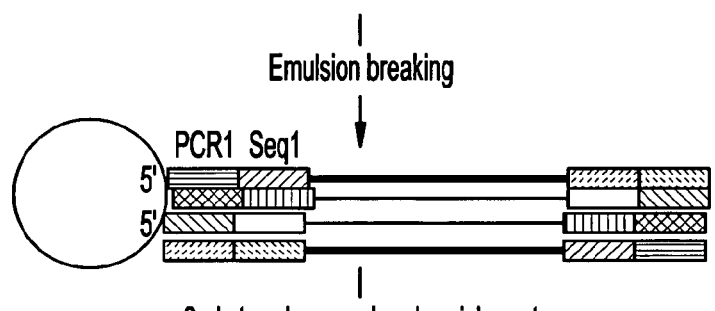
Figure 7C:
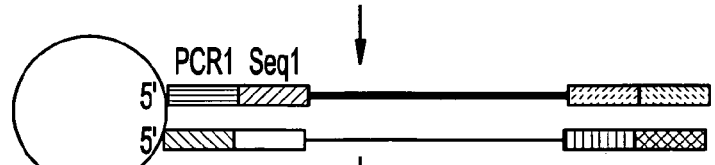
Figure 7D:
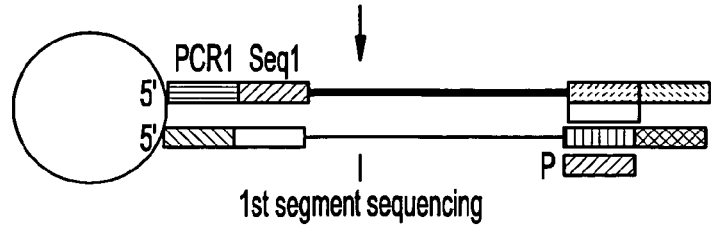
Figure 7E:
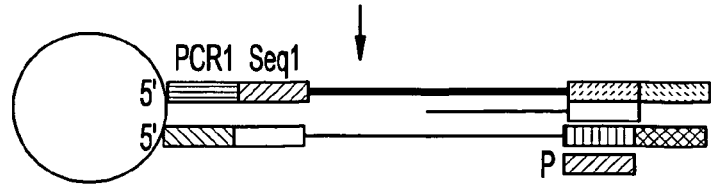

The emulsion was aliquotted into 7-8 separate PCR tubes. Each tube included approximately 75 µl of the emulsion. The tubes were sealed and placed in a MJ thermocycler along with the 25 µl negative control described above. The following cycle times were used: 1 cycle of incubation for 4 minutes at 94° C. (Hotstart Initiation), 30 cycles of incubation for 30 seconds at 94° C., and 150 seconds at 68° C. ( Amplification), and 40 cycles of incubation for 30 seconds at 94° C., and 360 seconds at 68° C. (Hybridization and Extension). After completion of the PCR program, the tubes were removed and the emulsions were broken immediately or the reactions were stored at 10° C. for up to 16 hours prior to initiating the breaking process. See FIG. 6.

Example 7

Breaking the Emulsion and Bead Recovery

Following amplification, the emulsifications were examined for breakage (separation of the oil and water phases). Unbroken emulsions were combined into a single 1.5 ml microcentrifuge tube, while the occasional broken emulsion was discarded. As the emulsion samples were quite viscous, significant amounts remained in each PCR tube. The emulsion remaining in the tubes was recovered by adding 75 µl of mineral oil into each PCR tube and pipetting the mixture. This mixture was added to the 1.5 ml tube containing the bulk of the emulsified material. The 1.5 ml tube was then vortexed for 30 seconds. After this, the tube was centrifuged for 20 minutes in the benchtop microcentrifuge at 13.2K rpm (full speed).

After centrifugation, the emulsion separated into two phases with a large white interface. The clear, upper oil phase was discarded, while the cloudy interface material was left in the tube. In a chemical fume hood, 1 ml hexanes was added to the lower phase and interface layer. The mixture was vortexed for 1 minute and centrifuged at full speed for 1 minute in a benchtop microcentrifuge. The top, oil/hexane phase was removed and discarded. After this, 1 ml of 80% Ethanol/1× Annealing Buffer was added to the remaining aqueous phase, interface, and beads. This mixture was vortexed for 1 minute or until the white material from the interface was dissolved. The sample was then centrifuged in a benchtop microcentrifuge for 1 minute at full speed. The tube was rotated 180 degrees, and spun again for an additional minute. The supernatant was then carefully removed without disturbing the bead pellet.

The white bead pellet was washed twice with 1 ml Annealing Buffer containing 0.1% Tween 20. The wash solution was discarded and the beads were pelleted after each wash as described above. The pellet was washed with 1 ml Picopure water. The beads were pelleted with the centrifuge-rotate-centrifuge method used previously. The aqueous phase was carefully removed. The beads were then washed with 1 ml of 1 mM EDTA as before, except that the beads were briefly vortexed at a medium setting for 2 seconds prior to pelleting and supernatant removal.

Amplified DNA, immobilized on the capture beads, was treated to obtain single stranded DNA. The second strand was removed by incubation in a basic melt solution. One ml of Melt Solution (0.125 M NaOH, 0.2 M NaCl) was subsequently added to the beads. The pellet was resuspended by vortexing at a medium setting for 2 seconds, and the tube placed in a Thermolyne LabQuake tube roller for 3 minutes. The beads were then pelleted as above, and the supernatant was carefully removed and discarded. The residual Melt solution was neutralized by the addition of 1 ml Annealing Buffer. After this, the beads were vortexed at medium speed for 2 seconds. The beads were pelleted, and the supernatant was removed as before. The Annealing Buffer wash was repeated, except that only 800 µl of the Annealing Buffer was removed after centrifugation. The beads and remaining Annealing Buffer were transferred to a 0.2 ml PCR tube. The beads were used immediately or stored at 4° C. for up to 48 hours before continuing on to the enrichment process.

The process in this step is shown schematically in FIG. 7.

Example 8

Bead Enrichment

The bead mass included beads with amplified, immobilized DNA strands, and empty or null beads. As mentioned previously, it was calculated that 61% of the beads lacked template DNA during the amplification process. Enrichment was used to selectively isolate beads with template DNA, thereby maximizing sequencing efficiency. The enrichment process is described in detail below.

The single stranded beads from the previous example were pelleted with the centrifuge-rotate-centrifuge method, and as much supernatant as possible was removed without disturbing the beads. Fifteen microliters of Annealing Buffer were added to the beads, followed by 2 µl of 100 µM biotinylated, 40 base enrichment primer (5'-Biotin-tetraethyleneglycol spacers ccattcccagctcgtcttgccatctgt-tccctccctgtctcag-3'; SEQ ID NO:3). The primer was complimentary to the combined amplification and sequencing sites (each 20 bases in length) on the 3' end of the bead-immobilized template. The solution was mixed by vortexing at a medium setting for 2 seconds, and the enrichment primers were annealed to the immobilized DNA strands using a controlled denaturation/annealing program in an MJ thermocycler. The program consisted of the following cycle times and temperatures: incubation for 30 seconds at 65° C., decrease by 0.1° C./sec to 58° C., incubation for 90 seconds at 58° C., and hold at 10° C.

While the primers were annealing, Dynal MyOne™ streptavidin beads were resuspend by gentle swirling. Next, 20 µl of the MyOne™ beads were added to a 1.5 ml microcentrifuge tube containing 1 ml of Enhancing fluid (2 M NaCl, 10 mM Tris-HCl, 1 mM EDTA, pH 7.5). The MyOne bead mixture was vortexed for 5 seconds, and the tube was placed in a Dynal MPC-S magnet. The paramagnetic beads were pelleted against the side of the microcentrifuge tube. The supernatant was carefully removed and discarded without disturbing the MyOne™ beads. The tube was removed from the magnet, and 100 µl of enhancing fluid was added. The tube was vortexed for 3 seconds to resuspend the beads, and stored on ice until needed.

Upon completion of the annealing program, 100 µl of annealing buffer was added to the PCR tube containing the DNA capture beads and enrichment primer. The tube vortexed for 5 seconds, and the contents were transferred to a fresh 1.5 ml microcentrifuge tube. The PCR tube in which the enrichment primer was annealed to the capture beads was washed once with 200 µl of annealing buffer, and the wash solution was added to the 1.5 ml tube. The beads were washed three times with 1 ml of annealing buffer, vortexed for 2 seconds, and pelleted as before. The supernatant was carefully removed. After the third wash, the beads were washed twice with 1 ml of ice cold Enhancing fluid. The beads were vortexed, pelleted, and the supernatant was removed as before. The beads were resuspended in 150 µl ice cold Enhancing fluid and the bead solution was added to the washed MyOne™ beads.

The bead mixture was vortexed for 3 seconds and incubated at room temperature for 3 minutes on a LabQuake tube roller. The streptavidin-coated MyOne™ beads were bound to the biotinylated enrichment primers annealed to immobilized templates on the DNA capture beads. The beads were then centrifuged at 2,000 RPM for 3 minutes, after which the beads were vortexed with 2 second pulses until resuspended. The resuspended beads were placed on ice for 5 minutes. Following this, 500 µl of cold Enhancing fluid was added to the beads and the tube was inserted into a Dynal MPC-S magnet. The beads were left undisturbed for 60 seconds to allow pelleting against the magnet. After this, the supernatant with excess MyOne™ and null DNA capture beads was carefully removed and discarded.

The tube was removed from the MPC-S magnet, and 1 ml of cold enhancing fluid added to the beads. The beads were resuspended with gentle finger flicking. It was important not to vortex the beads at this time, as forceful mixing could break the link between the MyOne™ and DNA capture beads. The beads were returned to the magnet, and the supernatant removed. This wash was repeated three additional times to ensure removal of all null capture beads. To remove the annealed enrichment primers and MyOne™ beads, the DNA capture beads were resuspended in 400 µl of melting solution, vortexed for 5 seconds, and pelleted with the magnet. The supernatant with the enriched beads was transferred to a separate 1.5 ml microcentrifuge tube. For maximum recovery of the enriched beads, a second 400 µl aliquot of melting solution was added to the tube containing the MyOne™ beads. The beads were vortexed and pelleted as before. The supernatant from the second wash was removed and combined with the first bolus of enriched beads. The tube of spent MyOne™ beads was discarded.

The microcentrifuge tube of enriched DNA capture beads was placed on the Dynal MPC-S magnet to pellet any residual MyOne™ beads. The enriched beads in the supernatant were transferred to a second 1.5 ml microcentrifuge tube and centrifuged. The supernatant was removed, and the beads were washed 3 times with 1 ml of annealing buffer to neutralize the residual melting solution. After the third wash, 800 µl of the supernatant was removed, and the remaining beads and solution were transferred to a 0.2 ml PCR tube. The enriched beads were centrifuged at 2,000 RPM for 3 minutes and the supernatant decanted. Next, 20 µl of annealing buffer and 3 µl of two different 100 µM sequencing primers (5'-ccatctgttccctccctgtc-3'; SEQ ID NO:4; and 5'-cctatcccctgttgcgtgtc-3' phosphate; SEQ ID NO:5) were added. The tube was vortexed for 5 seconds, and placed in an MJ thermocycler for the following 4-stage annealing program: incubation for 5 minutes at 65° C., decrease by 0.1° C./sec to 50° C., incubation for 1 minute at 50° C., decrease by 0.1° C./sec to 40° C., hold at 40° C. for 1 minute, decrease by 0.1° C./sec to 15° C., and hold at 15° C.

Upon completion of the annealing program, the beads were removed from thermocycler and pelleted by centrifugation for 10 seconds. The tube was rotated 180°, and spun for an additional 10 seconds. The supernatant was decanted and discarded, and 200 µl of annealing buffer was added to the tube. The beads were resuspended with a 5 second vortex, and pelleted as before. The supernatant was removed, and the beads resuspended in 100 µl annealing buffer. At this point, the beads were quantitated with a Multisizer 3 Coulter Counter (Beckman Coulter). Beads were stored at 4° C. and were stable for at least 1 week.

Example 9

Double Strand Sequencing

Figure 8:
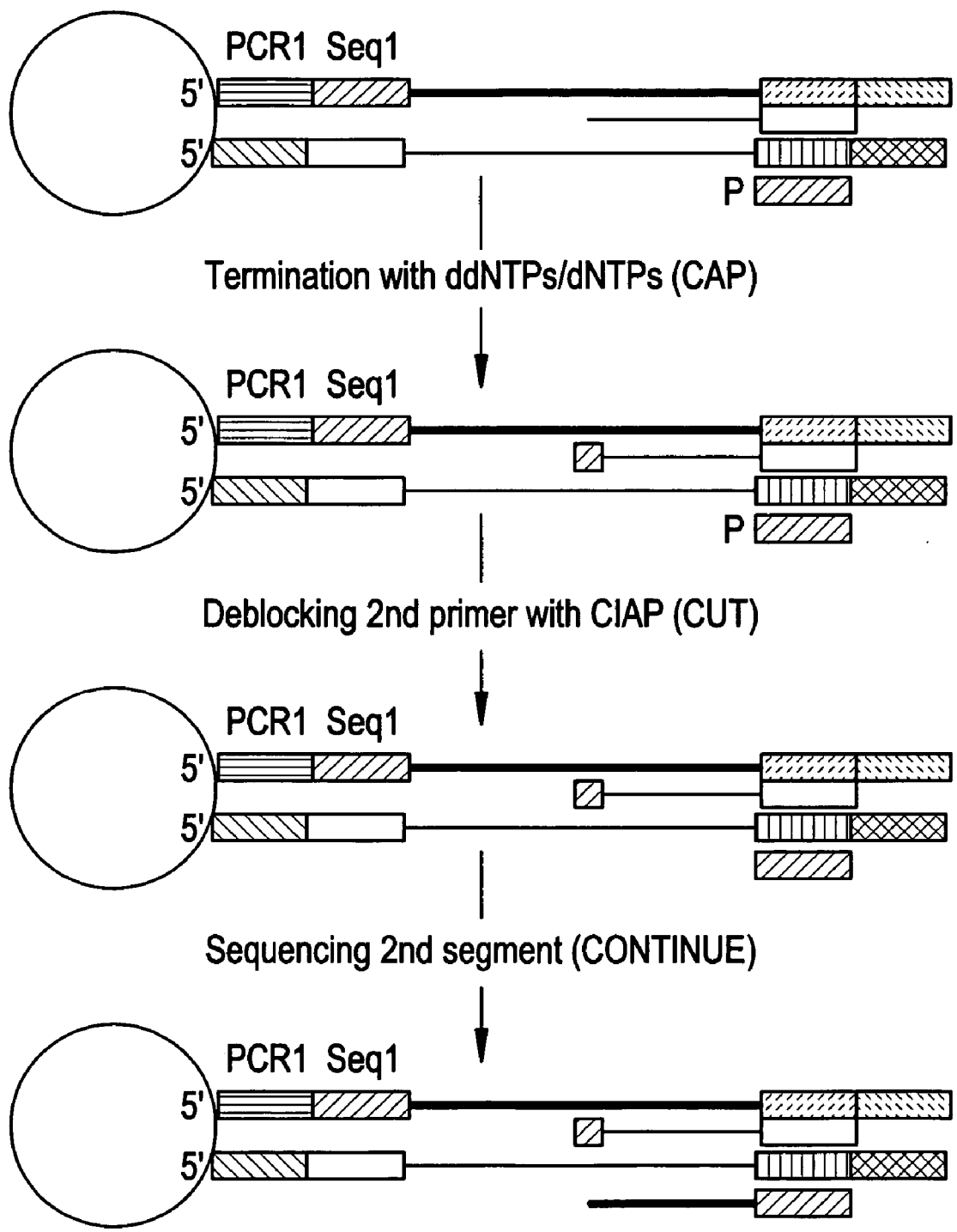
FIG. 8 is a schematic representation of a preferred method of double stranded sequencing.

For double strand sequencing, two different sequencing primers are used; an unmodified primer MMP7A and a 3' phosphorylated primer MMP2Bp. There are multiple steps in the process. This process is shown schematically in FIG. 8.

1) First Strand Sequencing. Sequencing of the first strand involves extension of the unmodified primer by a DNA polymerase through sequential addition of nucleotides for a predetermined number of cycles.

2) CAPPING: The first strand sequencing was terminated by flowing a Capping Buffer containing 25 mM Tricine, 5 mM Magnesium acetate, 1 mM DTT, 0.4 mg/ml PVP, 0.1 mg/ml BSA, 0.01% Tween and 2 µM of each dideoxynucleotides and 2 µM of each deoxynucleotide.

3) CLEAN: The residual deoxynucleotides and dideoxynucleotides was removed by flowing in Apyrase Buffer containing 25 mM Tricine, 5 mM Magnesium acetate, 1 mM DTT, 0.4 mg/ml PVP, 0.1 mg/ml BSA, 0.01% Tween and 8.5 units/L of Apyrase.

4) CUTTING: The second blocked primer was unblocked by removing the phosphate group from the 3' end of the modified 3' phosphorylated primer by flowing a Cutting buffer containing 5 units/ml of Calf intestinal phosphatases.

5) CONTINUE: The second unblocked primer was activated by addition of polymerase by flowing 1000 units/ml of DNA polymerases to capture all the available primer sites.

6) Second Strand Sequencing: Sequencing of the second strand by a DNA polymerase through sequential addition of nucleotides for a predetermined number of cycles.

Using the methods described above, the genomic DNA of *Staphylococcus aureus* was sequenced. The results are presented in FIG. 9. A total of 31,785 reads were obtained based on 15770 reads of the first strand and 16015 reads of the second strand. Of these, a total of 11,799 reads were paired and 8187 reads were unpaired obtaining a total coverage of 38%.

Read lengths ranged from 60 to 130 with an average of 95±9 bases (FIG. 10). The distribution of genome span and the number of wells of each genome span is shown in FIG. 11. Representative alignment strings, from this genomic sequencing, are shown in FIG. 12.

Throughout this specification, various patents, published patent applications and scientific references are cited to describe the state and content of the art. Those disclosures, in their entireties, are hereby incorporated into the present specification by reference.

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims.

We claim:

1. A method of sequencing a nucleic acid molecule comprising the steps of:
   (a) hybridizing two or more sequencing primers to one or a plurality of single strands of the nucleic acid molecule wherein all the primers except for one are reversibly blocked primers;
   (b) incorporating at least one base onto the nucleic acid molecule by polymerase elongation from an unblocked primer;
   (c) preventing further elongation of said unblocked primer
   (d) deblocking one of the reversibly blocked primers into an unblocked primer;
   (e) repeating steps (b) to (d) until at least one of the reversibly blocked primers are deblocked and used for determining a sequence.

2. The method of claim 1, wherein said step (c) of preventing further elongation comprises
   (a) completing the elongation from the unblocked primer with polymerase and dNTPs; or
   (b) terminating the elongation with polymerase in a manganese containing buffer, dNTPs, and at least one ddNTP; or
   (c) terminating the elongation chemically.

3. The method of claim 1 further comprising the step of removing said polymerase, dNTPs, and ddNTPs before said step (d).

4. The method of claim 1 wherein at least one reversibly blocked primer is blocked by a chemical moiety selected from the group consisting of a $PO_4$ group, a thio group, and a phosphorothiol group.

5. The method of claim 1 wherein at least one reversibly blocked primer has a 3' mismatched end that can be deblocked by contacting said primer with an exonuclease.

6. The method of claim 1 wherein at least one reversibly blocked primer has one or more noncomplementary bases that forms a loop and does not hybridize to the nucleic acid molecule, wherein said one or more bases is not at the 5' or 3' end of said reversibly blocked primer, and wherein said reversibly blocked primer comprises a dideoxy nucleotide at its 3' end.

7. The method of claim 6 wherein said at least one reversibly blocked primer is unblocked by endonuclease digestion of said one or more noncomplementary bases forming a nick at said one or more noncomplementary base.

8. The method of claim 7 wherein step (b) comprises polymerase elongation at said nick by a strand-displacing polymerase.

9. The method of claim 1 wherein at least one reversibly blocked primer has a sequence of 5'-NUX-3' wherein N represents an oligonucleotide sequence of any length, U is uracil, and X is a dideoxy-nucleotide.

10. The method of claim 9 wherein said reversibly blocked primer is unblocked by Uracil DNA glycosylase and AP endonuclease to generate an unblocked primer with an extendable 3' end.

11. The method of claim 1 at least one reversibly blocked primer has a sequence of 5'-NYZ-3' wherein N represents an oligonucleotide sequence of any length, Y is a modified nucleotide, and Z represents a single nucleotide base; and wherein said modified nucleotide can be deblocked by formamidopyrimidine (fapy)-DNA glycosylase.

12. The method of claim 11 wherein said modified base is selected from the group consisting of 8-oxoguanine, 8-oxoadenine, fapy-guanine, methyl-fapy-guanine, fapy-adenine, aflatoxin $B_1$-fapy-guanine, 5-hydroxy cytosine and 5-hydroxy-uracil.

13. The method of claim 1 wherein the nucleic acid molecule is a genomic DNA, cDNA, or episomal DNA.

14. The method of claim 1 wherein at least one sequencing primer hybridizes to a sense strand of the nucleic acid and at least one sequencing primer hybridizes to an antisense strand of the nucleic acid molecule in step (a).

15. The method of claim 1 wherein the polymerase elongation is between 1 and 250 bases.

16. The method of claim 1 wherein said method is performed in a reaction vessel selected from the group consisting of a test tube, a reaction chamber of a PicoTiter plate, a reaction chamber of an array, and a microencapsulated reaction chamber of a water-in-oil emulsion.

17. The method of claim 1 wherein the nucleic acid molecule is between 100 to 1000 bp in length.

18. The method of claim 1 wherein at least one said strand of nucleic acid molecule or at least one said primers is attached to a solid support.

19. The method of claim 1 wherein at least one strand of said nucleic acid molecule is linked to a solid support.

20. The method of claim 18, wherein at least one said primer is immobilized on a solid support to form an immobilized primer and said at least one strand is linked to a solid support by hybridization with said immobilized primer.

21. The method of claim 20 wherein the solid support is a spherical mobile solid support.

22. The method of claim 1 wherein at least one primer comprise a detectable label.

23. The method of claim 1 wherein the method of determining a sequence is pyrophosphate sequencing or Sanger sequencing.

24. The method of claim 1 wherein the deblocking step comprises contacting a reversibly blocked primer with an agent to remove a $PO_4$.group on said reversibly blocked primer.

25. The method of claim 24 wherein said agent is selected from the group consisting of polynucleotide kinase and alkaline phosphatase.

26. The method of claim 1 wherein said polymerase is devoid of 3' to 5' exonuclease activity.

27. The method of claim 1 wherein said method determines a first nucleic acid sequence proximate to one end of said nucleic acid molecule and a second nucleic acid sequence proximate to a second end of said nucleic acid molecule.

28. A method of sequencing a nucleic acid molecule comprising:
   (a) hybridizing a first unblocked sequencing primer to a first strand of the nucleic acid molecule;
   (b) hybridizing a second blocked sequencing primer to a second strand of the nucleic acid molecule;
   (c) incorporating at least one base onto said first strand by extending said first unblocked primer with a polymerase;
   (d) preventing further elongation of said unblocked primer;
   (e) deblocking the second sequencing primer; and
   (f) incorporating at least one base onto said second strand by extending said second primer with a polymerase;
   wherein steps (a) and (b) are performed in any order or simultaneously.

29. The method of claim 28, wherein said step (d) of preventing further elongation comprises
   (a) completing the elongation from the unblocked primer with polymerase and dNTPs; or (b) terminating the elongation with polymerase in a manganese containing buffer, dNTPs, and at least one ddNTP; or (c) terminating the elongation chemically.

30. The method of claim 29 further comprising the step of removing said polymerase, dNTPs, and ddNTPs after said preventing step.

31. The method of claim 28 wherein said second primer is blocked by a chemical moiety selected from the group consisting of a $PO_4$ group, a thio group, and a phosphorothiol group.

32. The method of claim 28 wherein said method determines at least a first nucleic acid sequence proximal to a first end of said nucleic acid molecule and determines a second nucleic acid sequence proximal to a second end of said nucleic acid molecule.

33. A method of determining a molecular haplotype of a DNA sample at multiple loci comprising the steps of:
(a) hybridizing 2 or more sequencing primers adjacent to a plurality of loci in a DNA sample wherein all the primers except for one are reversibly blocked primers and wherein each locus contains a nucleic acid sequence that determines a haplotype;
(b) determining a haplotype at one locus by polymerase elongation from an unblocked primer;
(c) preventing further elongation of said unblocked primer;
(d) deblocking one of the reversibly blocked primers into an unblocked primer;
(e) repeating steps (b) to (d) until all the reversibly blocked primers are deblocked and used for determining a molecular haplotype.

34. The method of claim 33, wherein said step (c) of preventing further elongation comprises
(a) completing the elongation from the unblocked primer with polymerase and dNTPs; or
(b) terminating the elongation with polymerase in a manganese containing buffer, dNTPs, and at least one ddNTP; or
(c) terminating the elongation chemically.

35. The method of claim 34 further comprising the step of removing said polymerase, dNTPs, and ddNTPs after said preventing step.

* * * * *

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial
<220> FEATURE:
<223> OTHER INFORMATION: Oligonucleotide

<400> SEQUENCE: 1
gcttacctga ccgacctctg                                           20

<210> SEQ ID NO 2
<211> LENGTH: 20
<212> TYPE: DNA
<213> ORGANISM: Artificial
<220> FEATURE:
<223> OTHER INFORMATION: Oligonucleotide

<400> SEQUENCE: 2
ccattcccca gctcgtcttg                                           20

<210> SEQ ID NO 3
<211> LENGTH: 44
<212> TYPE: DNA
<213> ORGANISM: Artificial
<220> FEATURE:
<223> OTHER INFORMATION: Oligonucleotide

<400> SEQUENCE: 3
ccattcccca gctcgtcttg ccatctgttc cctccctgtc tcag                 44

<210> SEQ ID NO 4
<211> LENGTH: 20
<212> TYPE: DNA
<213> ORGANISM: Artificial
<220> FEATURE:
<223> OTHER INFORMATION: Oligonucleotide

<400> SEQUENCE: 4
ccatctgttc cctccctgtc                                           20

<210> SEQ ID NO 5
<211> LENGTH: 20
<212> TYPE: DNA
<213> ORGANISM: Artificial
<220> FEATURE:
<223> OTHER INFORMATION: Oligonucleotide

<400> SEQUENCE: 5
cctatcccct gttgcgtgtc                                           20
```

```
-continued

<210> SEQ ID NO 6
<211> LENGTH: 23
<212> TYPE: DNA
<213> ORGANISM: Artificial
<220> FEATURE:
<223> OTHER INFORMATION: Oligonucleotide

<400> SEQUENCE: 6
atgcacatgg ttgacacagt ggt                                           23

<210> SEQ ID NO 7
<211> LENGTH: 22
<212> TYPE: DNA
<213> ORGANISM: Artificial
<220> FEATURE:
<223> OTHER INFORMATION: Oligonucleotide

<400> SEQUENCE: 7
atgcacatgg ttgacacagt gg                                            22

<210> SEQ ID NO 8
<211> LENGTH: 25
<212> TYPE: DNA
<213> ORGANISM: Artificial
<220> FEATURE:
<223> OTHER INFORMATION: Oligonucleotide

<400> SEQUENCE: 8
atgccaccga cctagtctca aactt                                         25

<210> SEQ ID NO 9
<211> LENGTH: 51
<212> TYPE: DNA
<213> ORGANISM: Artificial
<220> FEATURE:
<223> OTHER INFORMATION: Sequencing output

<400> SEQUENCE: 9
tattgttgat gctgtaaaaa gaagctactg gtgtagtatt tttatgaagt t            51

<210> SEQ ID NO 10
<211> LENGTH: 47
<212> TYPE: DNA
<213> ORGANISM: Artificial
<220> FEATURE:
<223> OTHER INFORMATION: Sequencing output

<400> SEQUENCE: 10
tgctcaaaga attcatttaa aatatgacca tatttcattg tatcttt                 47

<210> SEQ ID NO 11
<211> LENGTH: 48
<212> TYPE: DNA
<213> ORGANISM: Artificial
<220> FEATURE:
<223> OTHER INFORMATION: Sequencing output

<400> SEQUENCE: 11
aagcgaacag tcaagtacca cagtcagttg acttttacac aagcggat                48

<210> SEQ ID NO 12
<211> LENGTH: 47
<212> TYPE: DNA
<213> ORGANISM: Artificial
<220> FEATURE:
<223> OTHER INFORMATION: Sequencing output
```

<400> SEQUENCE: 12
tacaggtgtt ggtatgccat ttgcgatttg ttgcgcttgg ttagccg           47

<210> SEQ ID NO 13
<211> LENGTH: 52
<212> TYPE: DNA
<213> ORGANISM: Artificial
<220> FEATURE:
<223> OTHER INFORMATION: Sequencing output

<400> SEQUENCE: 13
aacatataaa catcccctat ctcaatttcc gcttccatgt aacaaaaaaa gc    52

<210> SEQ ID NO 14
<211> LENGTH: 38
<212> TYPE: DNA
<213> ORGANISM: Artificial
<220> FEATURE:
<223> OTHER INFORMATION: Sequencing output

<400> SEQUENCE: 14
tagatatcac ttgcgtgtta ctggtaagca ggcatgag                    38

<210> SEQ ID NO 15
<211> LENGTH: 41
<212> TYPE: DNA
<213> ORGANISM: Artificial
<220> FEATURE:
<223> OTHER INFORMATION: Sequencing output

<400> SEQUENCE: 15
attcaactct ggaaatgctt tcttgatacg cctcgatgat g                41

<210> SEQ ID NO 16
<211> LENGTH: 40
<212> TYPE: DNA
<213> ORGANISM: Artificial
<220> FEATURE:
<223> OTHER INFORMATION: Sequencing output

<400> SEQUENCE: 16
gatgaggagc tgcaatggca atgggttaaa ggcatcatcg                  40

<210> SEQ ID NO 17
<211> LENGTH: 45
<212> TYPE: DNA
<213> ORGANISM: Artificial
<220> FEATURE:
<223> OTHER INFORMATION: Sequencing output

<400> SEQUENCE: 17
tgtatctcga tttggattag ttgctttttg catcttcatt agacc            45

<210> SEQ ID NO 18
<211> LENGTH: 40
<212> TYPE: DNA
<213> ORGANISM: Artificial
<220> FEATURE:
<223> OTHER INFORMATION: Sequencing output

<400> SEQUENCE: 18
cattaacatc tgcaccagaa atagcttcta atacgattgc                  40

```
<210> SEQ ID NO 19
<211> LENGTH: 46
<212> TYPE: DNA
<213> ORGANISM: Artificial
<220> FEATURE:
<223> OTHER INFORMATION: Sequencing output

<400> SEQUENCE: 19
gcgacgacgt ccagctaata acgctgcacc taaggctaat gataat          46

<210> SEQ ID NO 20
<211> LENGTH: 43
<212> TYPE: DNA
<213> ORGANISM: Artificial
<220> FEATURE:
<223> OTHER INFORMATION: Sequencing output

<400> SEQUENCE: 20
aaaccatgca gatgctaaca aagctcaagc attaccagaa act              43

<210> SEQ ID NO 21
<211> LENGTH: 44
<212> TYPE: DNA
<213> ORGANISM: Artificial
<220> FEATURE:
<223> OTHER INFORMATION: Sequencing output

<400> SEQUENCE: 21
tgttgctgca tcataattta atactacatc atttaattct ttgg             44

<210> SEQ ID NO 22
<211> LENGTH: 51
<212> TYPE: DNA
<213> ORGANISM: Artificial
<220> FEATURE:
<223> OTHER INFORMATION: Sequencing output

<400> SEQUENCE: 22
gcagatggtg tgactaacca agttggtcaa aatgccctaa atacaaaaga t     51

<210> SEQ ID NO 23
<211> LENGTH: 39
<212> TYPE: DNA
<213> ORGANISM: Artificial
<220> FEATURE:
<223> OTHER INFORMATION: Oligonucleotide

<400> SEQUENCE: 23
gcttacctga ccgacctctg cctatcccct gttgcgtgt                   39

<210> SEQ ID NO 24
<211> LENGTH: 40
<212> TYPE: DNA
<213> ORGANISM: Artificial
<220> FEATURE:
<223> OTHER INFORMATION: Oligonucleotide

<400> SEQUENCE: 24
ccattcccca gctcgtcttg ccatctgttc cctccctgtc                  40
```